United States Patent [19]
Nakamura

[11] Patent Number: 6,013,767
[45] Date of Patent: Jan. 11, 2000

[54] BRAIN-SPECIFIC ADAPTER MOLECULE, GENE THEREOF, AND ANTIBODY THERETO

[75] Inventor: Takeshi Nakamura, Yokohama, Japan

[73] Assignee: Sumitomo Electric Industries, Ltd., Oasaka, Japan

[21] Appl. No.: 08/729,416

[22] Filed: Oct. 11, 1996

[30] Foreign Application Priority Data

| Oct. 13, 1995 | [JP] | Japan | 7-265988 |
| Dec. 12, 1995 | [JP] | Japan | 7-323069 |
| Feb. 29, 1996 | [JP] | Japan | 8-069265 |
| Jul. 24, 1996 | [JP] | Japan | 8-212973 |

[51] Int. Cl.[7] .................................. C07K 14/47
[52] U.S. Cl. .......................................... 530/350
[58] Field of Search ............................. 530/350

[56] References Cited

PUBLICATIONS

Pelicci et al., A Novel Transforming Protein (SHC) with an SH2 Domain Is Implicated in Mitogenic Signal Transduction, Cell, vol. 70, 93–104, Jul. 10, 1992.

Blaikie et al., A Region in Shc distinct from the SH2 domain can bind Tyrosine–Phosphorylated growth factor receptors, J. Biol Chem, Dec. 23, 1994, 269 (51).

Pawson, T., Protein Modules and signalling networks, Nature, Feb. 16, 1995, 373 (6515) P573–80.

O'Bryan J. P. et al., A mammalian adaptor protein with conserved Src homology 2 and phosphotyrosine–binding domains is related to Shc and is specifically expressed in the brain, Proceedings of the Nat'l Acad. of Sci. of the U.S. of A., 93(7), 1996, 2729–2734.

Nakamura, T. et al., N–Shc: A neural–specific adapter molecule that mediates signaling from neurotrophin–Trk to Ras–MAPK pathway, Oncogene, 13(6), 1996, 1111–1112.

Pelicci, G. et al., A family of Shc related protein with conserved PTB, CH1 and SH2 regions, Oncogene, 13 (3) 1996, 663–641.

Pelicci et al., *Oncogene,* vol., 11 pp. 899–907, 1995.

Obermeier et al., *EMBO J.,* vol. 13, pp. 1585–1590, 1994.

Lewin, *Science,* vol. 237, p. 1570, 1987.

Rudinger, *Peptide Hormones,* (ed. Parsons), University Park Press, Baltimore, pp. 1–7, 1976.

Salgaller et al., *Cancer Immunol. Immunother.,* vol. 39, pp. 105–116, 1994.

*Primary Examiner*—Anthony C. Caputa
*Assistant Examiner*—Stephen Gucker
*Attorney, Agent, or Firm*—Pillsbury Madison & Sutro, LLP Intellectual Property Group

[57] ABSTRACT

A novel brain-specific adapter molecule, its gene, an antibody to it, and a method of utilizing the antibody are provided. This invention screened a normalized cDNA library using mRNA derived from the human cerebrum, isolated a gene encoding a novel factor, FC99 protein, involved in the signaling pathways in neurons of the brain, and clarified its base sequence as well as a protein encoded by the gene. The invention also isolated from a rat brain-derived cDNA library a gene encoding rat FC99 protein, and clarified its base sequence as well as a protein encoded by the gene. The invention further produced an antibody to the protein, and measured tyrosine kinase activity in a cell by use of the antibody.

12 Claims, 5 Drawing Sheets

```
FC99 : LGPGVTYVKYLGCIEVLRSMRSLDFSTRTQITREAISRVCEAVPGAK    76
Shc  : MGPGVSVLVRYMGCVEVLQSMRALDFNTRTQVTREAISLVCEAVPGAK    93

FC99 : GAFKKRKEPSKMLSSILGKSNLQFAGMSISIFISTASLNLRTPDSKQI   124
Shc  : GATRRRKECSRPLSSILGRSNLKFAGMPITLTVSTSSLNLMAADCKQI   141

FC99 : IANHHMRSISFASGGDPDTTDYVAYVAKDPVNRRACHILECCDGLAQD   172
Shc  : IANHHMQSISFASGGDPDTAEYVAYVAKDPVNQRACHILECPEGLAQD   189

FC99 : VIGSIGQAFELRFKQYLQCP    192
Shc  : VISTIGQAFELRFKQYLRNP    209
```

FIG. 1A

```
FC99 : WYQGEMSRKEAEGLLEKDGDELVRKSTTNPGSFVLTGMHNGQAKHLLL   426
Shc  : WFHGKLSRREAEALLQLNGDELVRESTTPGQYVLTGLQSGQPKHLLL   425

FC99 : VDPEGTIRTKDRVFDSISHLINHHLESSLPIVSAGSELCLQQPVERKQ   474
Shc  : VDPEGVVRTKDHRFESVSHLISYHMDNHLPIISAGSELCLQQPVERKL   473
```

FIG. 1B

SEQUENCE LISTING (1) GENERAL INFORMATION:

(iii) NUMBER OF SEQUENCES: 22

(2) INFORMATION FOR SEQ ID NO:1:

(i) SEQUENCE CHARACTERISTICS:
        (A) LENGTH:474 amino acids
        (B) TYPE:amino acid
        (D) TOPOLOGY:linear (ii) MOLECULE TYPE:peptide (xi) SEQUENCE DESCRIPTION:SEQ ID NO:1:

```
Met Ser Ala Ala Arg Lys Gly Arg Pro Gly Asp Glu Pro Leu Pro
              5                  10                  15

Arg Pro Pro Arg Gly Thr Pro His Ala Ser Asp Gln Val Leu Gly
             20                  25                  30

Pro Gly Val Thr Tyr Val Val Lys Tyr Leu Gly Cys Ile Glu Val
             35                  40                  45

Leu Arg Ser Met Arg Ser Leu Asp Phe Ser Thr Arg Thr Gln Ile
             50                  55                  60

Thr Arg Glu Ala Ile Ser Arg Val Cys Glu Ala Val Pro Gly Ala
             65                  70                  75

Lys Gly Ala Phe Lys Lys Arg Pro Pro Ser Lys Met Leu Ser
             80                  85                  90

Ser Ile Leu Gly Lys Ser Asn Leu Gln Phe Ala Gly Met Ser Ile
             95                 100                 105

Ser Leu Thr Ile Ser Thr Ala Ser Leu Asn Leu Arg Thr Pro Asp
            110                 115                 120

Ser Lys Gln Ile Ile Ala Asn His His Met Arg Ser Ile Ser Phe
            125                 130                 135

Ala Ser Gly Gly Asp Pro Asp Thr Thr Asp Tyr Val Ala Tyr Val
            140                 145                 150

Ala Lys Asp Pro Val Asn Arg Arg Ala Cys His Ile Leu Glu Cys
            155                 160                 165

Cys Asp Gly Leu Ala Gln Asp Val Ile Gly Ser Ile Gly Gln Ala
            170                 175                 180

Phe Glu Leu Arg Phe Lys Gln Tyr Leu Gln Cys Pro Thr Lys Ile
            185                 190                 195

Pro Ala Leu His Asp Arg Met Gln Ser Leu Asp Glu Pro Trp Thr
            200                 205                 210

Glu Glu Glu Gly Asp Gly Ser Asp His Pro Tyr Tyr Asn Ser Ile
            215                 220                 225

Pro Ser Lys Met Pro Pro Gly Gly Phe Leu Asp Thr Arg Leu
            230                 235                 240

Lys Pro Arg Pro His Ala Pro Asp Thr Ala Gln Phe Ala Gly Lys
            245                 250                 255

Glu Gln Thr Tyr Tyr Gln Gly Arg His Leu Gly Asp Thr Phe Gly
            260                 265                 270

Glu Asp Trp Gln Gln Thr Pro Leu Arg Gln Gly Ser Ser Asp Ile
            275                 280                 285

Tyr Ser Thr Pro Glu Gly Lys Leu His Val Ala Pro Thr Gly Glu
            290                 295                 300

Ala Pro Thr Tyr Val Asn Thr Gln Gln Ile Pro Pro Gln Ala Trp
            305                 310                 315

Pro Ala Ala Val Ser Ser Ala Glu Ser Ser Pro Arg Lys Asp Leu
            320                 325                 330

Phe Asp Met Lys Pro Phe Glu Asp Ala Leu Lys Asn Gln Pro Leu
            335                 340                 345
```

```
Gly Pro Val Leu Ser Lys Ala Ala Ser Val Glu Cys Ile Ser Pro
                350                 355                 360

Val Ser Pro Arg Ala Pro Asp Ala Lys Met Leu Glu Glu Leu Gln
                365                 370                 375

Ala Glu Thr Trp Tyr Gln Gly Glu Met Ser Arg Lys Glu Ala Glu
                380                 385                 390

Gly Leu Leu Glu Lys Asp Gly Asp Phe Leu Val Arg Lys Ser Thr
                395                 400                 405

Thr Asn Pro Gly Ser Phe Val Leu Thr Gly Met His Asn Gly Gln
                410                 415                 420

Ala Lys His Leu Leu Leu Val Asp Pro Glu Gly Thr Ile Arg Thr
                425                 430                 435

Lys Asp Arg Val Phe Asp Ser Ile Ser His Leu Ile Asn His His
                440                 445                 450

Leu Glu Ser Ser Leu Pro Ile Val Ser Ala Gly Ser Glu Leu Cys
                455                 460                 465

Leu Gln Gln Pro Val Glu Arg Lys Gln
                470

(2) INFORMATION FOR SEQ ID NO:2:

(i) SEQUENCE CHARACTERISTICS:
        (A) LENGTH:1425 base pairs
        (B) TYPE:nucleic acid
        (C) STRANDEDNESS:double strand
        (D) TOPOLOGY:linear (ii) MOLECULE TYPE:cDNA to mRNA (xi) SEQUENCE DESCRIPTION:SEQ ID NO:2:

ATG AGC GCC GCC AGG AAG GGC CGG CCC GGC GAC GAG CCG CTG CCC         45

AGG CCC CCT CGG GGG ACG CCG CAC GCC AGC GAC CAG GTG CTG GGG         90

CCC GGA GTC ACC TAC GTG GTC AAG TAC TTG GGG TGC ATT GAA GTT        135

CTG CGC TCA ATG AGG TCT CTT GAC TTC AGT ACA AGA ACA CAA ATT        180

ACC AGG GAA GCC ATC AGC CGC GTC TGT GAA GCT GTG CCT GGT GCG        225

AAG GGA GCC TTC AAG AAG AGA AAG CCT CCA AGC AAA ATG CTG TCC        270

AGC ATC TTG GGA AAG AGC AAC CTC CAG TTT GCG GGA ATG AGC ATC        315

TCT CTG ACC ATC TCC ACG GCC AGT CTG AAC CTG CGA ACT CCG GAC        360

TCC AAA CAG ATC ATA GCG AAT CAC CAC ATG CGG TCC ATC TCC TTC        405

GCC TCT GGG GGA GAC CCG GAC ACA ACT GAC TAT GTT GCA TAT GTG        450

GCT AAG GAC CCT GTT AAT CGC AGA GCT TGT CAC ATT TTG GAA TGC        495

TGT GAT GGG CTG GCC CAG GAT GTC ATC GGC TCC ATC GGA CAA GCC        540

TTT GAG CTC CGG TTT AAG CAA TAT TTA CAG TGT CCT ACC AAG ATT        585

CCC GCT CTC CAT GAT CGA ATG CAG AGT CTG GAT GAG CCA TGG ACG        630

GAA GAG GAG GGA GAT GGC TCA GAC CAC CCA TAC TAC AAC AGC ATC        675

CCA AGC AAG ATG CCT CCT CCA GGG GGC TTT CTT GAT ACT AGA CTG        720

AAA CCC AGA CCC CAT GCT CCT GAC ACA GCC CAG TTT GCA GGA AAA        765

GAG CAG ACT TAT TAC CAG GGA AGA CAC TTA GGA GAC ACT TTT GGC        810

GAA GAC TGG CAG CAA ACA CCT TTA AGG CAA GGG TCC TCG GAC ATC        855

TAC AGC ACG CCA GAA GGG AAA CTG CAC GTG GCC CCC ACG GGA GAA        900
```

| | |
|---|---|
| GCA CCC ACC TAC GTC AAC ACT CAG CAG ATC CCA CCA CAG GCC TGG | 945 |
| CCG GCT GCG GTC AGC AGT GCT GAG AGC AGC CCG AGG AAA GAC CTC | 990 |
| TTT GAC ATG AAA CCT TTT GAA GAT GCT CTC AAG AAC CAG CCC TTG | 1035 |
| GGG CCC GTG TTA AGC AAG GCA GCC TCC GTG GAG TGC ATC AGC CCT | 1080 |
| GTG TCA CCT AGA GCC CCA GAT GCC AAG ATG CTG GAG GAA CTG CAA | 1125 |
| GCC GAG ACT TGG TAC CAA GGA GAG ATG AGC AGG AAG GAG GCA GAG | 1170 |
| GGG CTG CTG GAG AAA GAC GGA GAC TTC CTG GTC AGG AAG AGC ACC | 1215 |
| ACC AAC CCG GGC TCC TTT GTC CTC ACG GGC ATG CAC AAT GGC CAG | 1260 |
| GCC AAG CAC CTG CTG CTC GTG GAC CCA GAA GGC ACG ATC CGG ACA | 1305 |
| AAG GAC AGA GTC TTT GAC AGT ATC AGC CAC CTC ATC AAC CAC CAC | 1350 |
| CTA GAA AGC AGC CTG CCC ATT GTC TCT GCA GGG AGT GAG CTG TGT | 1395 |
| CTC CAG CAG CCA GTG GAG AGG AAG CAG TGA | 1425 |

(2) INFORMATION FOR SEQ ID NO:3:

(i) SEQUENCE CHARACTERISTICS:
        (A) LENGTH:164 amino acids
        (B) TYPE:amino acid
        (D) TOPOLOGY:linear (ii) MOLECULE TYPE:peptide (xi) SEQUENCE DESCRIPTION:SEQ ID NO:3:

Leu Gly Pro Gly Val Thr Tyr Val Val Lys Tyr Leu Gly Cys Ile
             5                      10                    15

Glu Val Leu Arg Ser Met Arg Ser Leu Asp Phe Ser Thr Arg Thr
            20                      25                    30

Gln Ile Thr Arg Glu Ala Ile Ser Arg Val Cys Glu Ala Val Pro
            35                      40                    45

Gly Ala Lys Gly Ala Phe Lys Lys Arg Lys Pro Pro Ser Lys Met
            50                      55                    60

Leu Ser Ser Ile Leu Gly Lys Ser Asn Leu Gln Phe Ala Gly Met
            65                      70                    75

Ser Ile Ser Leu Thr Ile Ser Thr Ala Ser Leu Asn Leu Arg Thr
            80                      85                    90

Pro Asp Ser Lys Gln Ile Ile Ala Asn His His Met Arg Ser Ile
            95                      100                 105

Ser Phe Ala Ser Gly Gly Asp Pro Asp Thr Thr Asp Tyr Val Ala
            110                    115                120

Tyr Val Ala Lys Asp Pro Val Asn Arg Arg Ala Cys His Ile Leu
            125                    130                135

Glu Cys Cys Asp Gly Leu Ala Gln Asp Val Ile Gly Ser Ile Gly
            140                    145                150

Gln Ala Phe Glu Leu Arg Phe Lys Gln Tyr Leu Gln Cys Pro
            155                    160

(2) INFORMATION FOR SEQ ID NO:4:

(i) SEQUENCE CHARACTERISTICS:
        (A) LENGTH:492 base pairs
        (B) TYPE:nucleic acid
        (C) STRANDEDNESS:double strand
        (D) TOPOLOGY:linear (ii) MOLECULE TYPE:cDNA to mRNA (xi) SEQUENCE DESCRIPTION:SEQ ID NO:4:

```
CTG GGG CCC GGA GTC ACC TAC GTG GTC AAG TAC TTG GGG TGC ATT        45
GAA GTT CTG CGC TCA ATG AGG TCT CTT GAC TTC AGT ACA AGA ACA        90
CAA ATT ACC AGG GAA GCC ATC AGC CGC GTC TGT GAA GCT GTG CCT       135
GGT GCG AAG GGA GCC TTC AAG AAG AGA AAG CCT CCA AGC AAA ATG       180
CTG TCC AGC ATC TTG GGA AAG AGC AAC CTC CAG TTT GCG GGA ATG       225
AGC ATC TCT CTG ACC ATC TCC ACG GCC AGT CTG AAC CTG CGA ACT       270
CCG GAC TCC AAA CAG ATC ATA GCG AAT CAC CAC ATG CGG TCC ATC       315
TCC TTC GCC TCT GGG GGA GAC CCG GAC ACA ACT GAC TAT GTT GCA       360
TAT GTG GCT AAG GAC CCT GTT AAT CGC AGA GCT TGT CAC ATT TTG       405
GAA TGC TGT GAT GGG CTG GCC CAG GAT GTC ATC GGC TCC ATC GGA       450
CAA GCC TTT GAG CTC CGG TTT AAG CAA TAT TTA CAG TGT CCT           492
```

(2) INFORMATION FOR SEQ ID NO:5:

(i) SEQUENCE CHARACTERISTICS:
        (A) LENGTH:96 amino acids
        (B) TYPE:amino acid
        (D) TOPOLOGY:linear (ii) MOLECULE TYPE:peptide (xi) SEQUENCE DESCRIPTION:SEQ ID NO:5:

```
Trp Tyr Gln Gly Glu Met Ser Arg Lys Glu Ala Glu Gly Leu Leu
                  5                  10                  15
Glu Lys Asp Gly Asp Phe Leu Val Arg Lys Ser Thr Thr Asn Pro
                 20                  25                  30
Gly Ser Phe Val Leu Thr Gly Met His Asn Gly Gln Ala Lys His
                 35                  40                  45
Leu Leu Leu Val Asp Pro Glu Gly Thr Ile Arg Thr Lys Asp Arg
                 50                  55                  60
Val Phe Asp Ser Ile Ser His Leu Ile Asn His His Leu Glu Ser
                 65                  70                  75
Ser Leu Pro Ile Val Ser Ala Gly Ser Glu Leu Cys Leu Gln Gln
                 80                  85                  90
Pro Val Glu Arg Lys Gln
                 95
```

(2) INFORMATION FOR SEQ ID NO:6:

(i) SEQUENCE CHARACTERISTICS:
        (A) LENGTH:288 base pairs
        (B) TYPE:nucleic acid
        (C) STRANDEDNESS:double strand
        (D) TOPOLOGY:linear (ii) MOLECULE TYPE:cDNA to mRNA (xi) SEQUENCE DESCRIPTION:SEQ ID NO:6:

```
TGG TAC CAA GGA GAG ATG AGC AGG AAG GAG GCA GAG GGG CTG CTG        45
GAG AAA GAC GGA GAC TTC CTG GTC AGG AAG AGC ACC ACC AAC CCG        90
GGC TCC TTT GTC CTC ACG GGC ATG CAC AAT GGC CAG GCC AAG CAC       135
CTG CTG CTC GTG GAC CCA GAA GGC ACG ATC CGG ACA AAG GAC AGA       180
GTC TTT GAC AGT ATC AGC CAC CTC ATC AAC CAC CAC CTA GAA AGC       225
```

```
AGC CTG CCC ATT GTC TCT GCA GGG AGT GAG CTG TGT CTC CAG CAG         270

CCA GTG GAG AGG AAG CAG                                              288
```

(2) INFORMATION FOR SEQ ID NO:7:

(i) SEQUENCE CHARACTERISTICS:
        (A) LENGTH:594 amino acids
        (B) TYPE:amino acid
        (D) TOPOLOGY:linear (ii) MOLECULE TYPE:peptide (xi) SEQUENCE DESCRIPTION:SEQ ID NO:7:

```
Met Leu Pro Arg Thr Lys Tyr Asn Arg Phe Arg Asn Asp Ser Val
                  5                  10                  15

Thr Ser Val Asp Asp Leu Leu His Ser Leu Ser Val Ser Gly Gly
                 20                  25                  30

Gly Gly Lys Val Ser Ala Ala Arg Ala Thr Pro Ala Ala Ala Pro
                 35                  40                  45

Tyr Leu Val Ser Gly Glu Ala Leu Arg Lys Ala Pro Asp Asp Gly
                 50                  55                  60

Pro Gly Ser Leu Gly His Leu Leu His Lys Val Ser His Leu Lys
                 65                  70                  75

Leu Ser Ser Ser Gly Leu Arg Gly Leu Ser Ser Ala Ala Arg Glu
                 80                  85                  90

Arg Ala Gly Ala Arg Leu Ser Gly Ser Cys Ser Ala Pro Ser Leu
                 95                 100                 105

Ala Ala Pro Asp Gly Ser Ala Pro Ser Ala His Arg Ala Pro Ala
                110                 115                 120

Met Ser Ala Ala Arg Lys Gly Arg Pro Gly Asp Glu Pro Leu Pro
                125                 130                 135

Arg Pro Pro Arg Gly Thr Pro His Ala Ser Asp Gln Val Leu Gly
                140                 145                 150

Pro Gly Val Thr Tyr Val Val Lys Tyr Leu Gly Cys Ile Glu Val
                155                 160                 165

Leu Arg Ser Met Arg Ser Leu Asp Phe Ser Thr Arg Thr Gln Ile
                170                 175                 180

Thr Arg Glu Ala Ile Ser Arg Val Cys Glu Ala Val Pro Gly Ala
                185                 190                 195

Lys Gly Ala Phe Lys Lys Arg Lys Pro Pro Ser Lys Met Leu Ser
                200                 205                 210

Ser Ile Leu Gly Lys Ser Asn Leu Gln Phe Ala Gly Met Ser Ile
                215                 220                 225

Ser Leu Thr Ile Ser Thr Ala Ser Leu Asn Leu Arg Thr Pro Asp
                230                 235                 240

Ser Lys Gln Ile Ile Ala Asn His His Met Arg Ser Ile Ser Phe
                245                 250                 255

Ala Ser Gly Gly Asp Pro Asp Thr Thr Asp Tyr Val Ala Tyr Val
                260                 265                 270

Ala Lys Asp Pro Val Asn Arg Arg Ala Cys His Ile Leu Glu Cys
                275                 280                 285

Cys Asp Gly Leu Ala Gln Asp Val Ile Gly Ser Ile Gly Gln Ala
                290                 295                 300

Phe Glu Leu Arg Phe Lys Gln Tyr Leu Gln Cys Pro Thr Lys Ile
                305                 310                 315

Pro Ala Leu His Asp Arg Met Gln Ser Leu Asp Glu Pro Trp Thr
```

```
                    320                 325                 330
Glu Glu Glu Gly Asp Gly Ser Asp His Pro Tyr Tyr Asn Ser Ile
                335                 340                 345
Pro Ser Lys Met Pro Pro Gly Gly Phe Leu Asp Thr Arg Leu
            350                 355                 360
Lys Pro Arg Pro His Ala Pro Asp Thr Ala Gln Phe Ala Gly Lys
            365                 370                 375
Glu Gln Thr Tyr Tyr Gln Gly Arg His Leu Gly Asp Thr Phe Gly
            380                 385                 390
Glu Asp Trp Gln Gln Thr Pro Leu Arg Gln Gly Ser Ser Asp Ile
            395                 400                 405
Tyr Ser Thr Pro Glu Gly Lys Leu His Val Ala Pro Thr Gly Glu
            410                 415                 420
Ala Pro Thr Tyr Val Asn Thr Gln Gln Ile Pro Pro Gln Ala Trp
            425                 430                 435
Pro Ala Ala Val Ser Ser Ala Glu Ser Ser Pro Arg Lys Asp Leu
            440                 445                 450
Phe Asp Met Lys Pro Phe Glu Asp Ala Leu Lys Asn Gln Pro Leu
            455                 460                 465
Gly Pro Val Leu Ser Lys Ala Ala Ser Val Glu Cys Ile Ser Pro
            470                 475                 480
Val Ser Pro Arg Ala Pro Asp Ala Lys Met Leu Glu Glu Leu Gln
            485                 490                 495
Ala Glu Thr Trp Tyr Gln Gly Glu Met Ser Arg Lys Glu Ala Glu
            500                 505                 510
Gly Leu Leu Glu Lys Asp Gly Asp Phe Leu Val Arg Lys Ser Thr
            515                 520                 525
Thr Asn Pro Gly Ser Phe Val Leu Thr Gly Met His Asn Gly Gln
            530                 535                 540
Ala Lys His Leu Leu Leu Val Asp Pro Glu Gly Thr Ile Arg Thr
            545                 550                 555
Lys Asp Arg Val Phe Asp Ser Ile Ser His Leu Ile Asn His His
            560                 565                 570
Leu Glu Ser Ser Leu Pro Ile Val Ser Ala Gly Ser Glu Leu Cys
            575                 580                 585
Leu Gln Gln Pro Val Glu Arg Lys Gln
            590

(2) INFORMATION FOR SEQ ID NO:8:

(i) SEQUENCE CHARACTERISTICS:
        (A) LENGTH:1785 base pairs
        (B) TYPE:nucleic acid
        (C) STRANDEDNESS:double strand
        (D) TOPOLOGY:linear (ii) MOLECULE TYPE:cDNA to mRNA (xi) SEQUENCE DESCRIPTION:SEQ ID NO:8:

ATG CTT CCA CGC ACC AAG TAT AAC CGC TTC AGG AAT GAC TCG GTG        45

ACA TCG GTC GAT GAC CTT CTC CAC AGC CTG TCG GTG AGC GGC GGC        90

GGA GGC AAG GTT TCG GCG GCG CGC GCG ACC CCG GCG GCG GCT CCC       135

TAC TTG GTG TCC GGC GAG GCG CTG CGC AAG GCG CCC GAC GAT GGG       180

CCC GGC AGC CTG GGC CAC CTG CTC CAC AAG GTG TCC CAC CTG AAA       225

CTC TCC AGC TCG GGC CTC CGC GGC CTG TCG TCG GCC GCC CGG GAG       270
```

```
CGG GCG GGC GCG CGG CTC TCG GGC AGC TGC AGC GCG CCC AGC CTG          315

GCC GCC CCG GAC GGC AGT GCG CCC TCG GCG CAC CGC GCC CCG GCC          360

ATG AGC GCC GCC AGG AAG GGC CGG CCC GGC GAC GAG CCG CTG CCC          405

AGG CCC CCT CGG GGG ACG CCG CAC GCC AGC GAC CAG GTG CTG GGG          450

CCC GGA GTC ACC TAC GTG GTC AAG TAC TTG GGG TGC ATT GAA GTT          495

CTG CGC TCA ATG AGG TCT CTT GAC TTC AGT ACA AGA ACA CAA ATT          540

ACC AGG GAA GCC ATC AGC CGC GTC TGT GAA GCT GTG CCT GGT GCG          585

AAG GGA GCC TTC AAG AAG AGA AAG CCT CCA AGC AAA ATG CTG TCC          630

AGC ATC TTG GGA AAG AGC AAC CTC CAG TTT GCG GGA ATG AGC ATC          675

TCT CTG ACC ATC TCC ACG GCC AGT CTG AAC CTG CGA ACT CCG GAC          720

TCC AAA CAG ATC ATA GCG AAT CAC CAC ATG CGG TCC ATC TCC TTC          765

GCC TCT GGG GGA GAC CCG GAC ACA ACT GAC TAT GTT GCA TAT GTG          810

GCT AAG GAC CCT GTT AAT CGC AGA GCT TGT CAC ATT TTG GAA TGC          855

TGT GAT GGG CTG GCC CAG GAT GTC ATC GGC TCC ATC GGA CAA GCC          900

TTT GAG CTC CGG TTT AAG CAA TAT TTA CAG TGT CCT ACC AAG ATT          945

CCC GCT CTC CAT GAT CGA ATG CAG AGT CTG GAT GAG CCA TGG ACG          990

GAA GAG GAG GGA GAT GGC TCA GAC CAC CCA TAC TAC AAC AGC ATC         1035

CCA AGC AAG ATG CCT CCT CCA GGG GGC TTT CTT GAT ACT AGA CTG         1080

AAA CCC AGA CCC CAT GCT CCT GAC ACA GCC CAG TTT GCA GGA AAA         1125

GAG CAG ACT TAT TAC CAG GGA AGA CAC TTA GGA GAC ACT TTT GGC         1170

GAA GAC TGG CAG CAA ACA CCT TTA AGG CAA GGG TCC TCG GAC ATC         1215

TAC AGC ACG CCA GAA GGG AAA CTG CAC GTG GCC CCC ACG GGA GAA         1260

GCA CCC ACC TAC GTC AAC ACT CAG CAG ATC CCA CCA CAG GCC TGG         1305

CCG GCT GCG GTC AGC AGT GCT GAG AGC AGC CCG AGG AAA GAC CTC         1350

TTT GAC ATG AAA CCT TTT GAA GAT GCT CTC AAG AAC CAG CCC TTG         1395

GGG CCC GTG TTA AGC AAG GCA GCC TCC GTG GAG TGC ATC AGC CCT         1440

GTG TCA CCT AGA GCC CCA GAT GCC AAG ATG CTG GAG GAA CTG CAA         1485

GCC GAG ACT TGG TAC CAA GGA GAG ATG AGC AGG AAG GAG GCA GAG         1530

GGG CTG CTG GAG AAA GAC GGA GAC TTC CTG GTC AGG AAG AGC ACC         1575

ACC AAC CCG GGC TCC TTT GTC CTC ACG GGC ATG CAC AAT GGC CAG         1620

GCC AAG CAC CTG CTG CTC GTG GAC CCA GAA GGC ACG ATC CGG ACA         1665

AAG GAC AGA GTC TTT GAC AGT ATC AGC CAC CTC ATC AAC CAC CAC         1710

CTA GAA AGC AGC CTG CCC ATT GTC TCT GCA GGG AGT GAG CTG TGT         1755

CTC CAG CAG CCA GTG GAG AGG AAG CAG TGA                             1785
```

(2) INFORMATION FOR SEQ ID NO:9:

(i) SEQUENCE CHARACTERISTICS:
        (A) LENGTH:422 base pairs
        (B) TYPE:nucleic acid
        (C) STRANDEDNESS:double strand
        (D) TOPOLOGY:linear (ii) MOLECULE TYPE:cDNA to mRNA (xi) SEQUENCE DESCRIPTION:SEQ ID NO:9:

```
TTGACTTCAG TACAAGAACA CAAATTACCA GGGAAGCCAT CAGCCGCGTC TGTGAAGCTG        60

TGCCTGGTGC GAAGGGAGCC TTCAAGAAGA GAAAGCCTCC AAGCAAAATG CTGTCCAGCA       120

TCTTGGGAAA GAGCAACCTC CAGTTTGCGG GAATGAGCAT CTCTCTGACC ATCTCCACGG       180

CCAGTCTGAA CCTGCGAACT CCGGACTCCA AACAGATCAT AGCGAATCAC ACATGCGGT        240

CCATCTCCTT CGCCTCTGGG GGAGACCCGG ACACAACTGA CTATGTTGCA TATGTGGCTA       300

AGGACCCTGT TAATCGCAGA GCTTGTCACA TTTTGGAATG CTGTGATGGG CTGGCCCAGG       360

ATGTCATCGG CTCCATCGGA CAAGCCTTTG AGCTCCGGTT TAAGCAATAT TTACAGTGTC       420

CT                                                                     422
```

(2) INFORMATION FOR SEQ ID NO:10:

(i) SEQUENCE CHARACTERISTICS:
        (A) LENGTH:1425 base pairs
        (B) TYPE:nucleic acid
        (C) STRANDEDNESS:double strand
        (D) TOPOLOGY:linear (ii) MOLECULE TYPE:cDNA to mRNA (xi) SEQUENCE DESCRIPTION:SEQ ID NO:10:

```
ATG AGC GCC ACC AGG AAG AGC CGG GCC AGC GAC GAG CCG TTG CCC             45

AGG CCC CCG CGG GGC GCG CCG CAC GCC AGC GAC CAG GTG CTG GGG             90

TCG GGA GTC ACC TAT GTG GTC AAG TAC TTG GGA TGC ATC GAA GTT            135

CTG CGC TCA ATG AGG TCT CTT GAC TTC AGT ACA AGA ACT CAG GTT            180

ACC AGG GAA GCC ATC AGC CGT GTC TGC GAA GCT GTG CCA GGC GCC            225

AAA GGA GCC TTC AAG AAG AGA AAG CCT CCG AGT AAA ATG CTG TCC            270

AGC ATC CTG GGG AAG AGC AAC CTC CAG TTC GCA GGG ATG AGC ATC            315

TCC CTG ACC ATC TCC ACC GCC AGC CTG AAC CTG CGC ACT CCT GAC            360

TCC AAA CAG ATC ATA TCG AAC CAT CAC ATG CGG TCC ATC TCC TTC            405

GCC TCA GGG GGA GAC CCG GAC ACA ACA GAC TAT GTT GCC TAC GTC            450

GCT AAG GAC CCT GTG AAT CGC AGA GCT TGC CAC ATT CTG GAA TGC            495

TGT GAC GGG CTA GCC CAA GAT GTC ATC GGC TCC ATC GGA CAA GCC            540

TTT GAA CTC CGG TTC AAG CAG TAT TTG CAG TGT CCT TCC AAG ATT            585

CCT GCT CTC CAG GAC CGA ATG CAG AGT CTG GAC GAG CCG TGG ACT            630

GAA GAA GAG GGA GAT GGC CCC GAT CAC CCG TAC TAC AAC AGC GTT            675

CCC AAC AAG ATG CCT CCT CCA GGA GGG TTT CTC GAT GCT CGA TTG            720

AAA GCC AGA CCC CAC GCA CCT GAT GCA GCC CAG TTT TCA GGA AAA            765

GAG CAA ACT TAT TAC CAG GGA AGA CAC TTA GGA GAT GCA TTC GGT            810

GAA GAC TGG CAG AGA GCA CCC ACC AGG CAA GGC TCC TTG GAC ATC            855

TAT AGC ACA CCA GAA GGG AAA GCT CAC ATG GTT CCT GTA GGA GAA            900

ACA CCA ACC TAT GTC AAC ACC CAG CCA GTC CCA CCA CAG GTT TGG            945

CCA GCA GCA ACC AGC AGC ACT GAG AGC AGC CCA CGG AAG GAC CTC            990

TTT GAC ATG AAG CCT TTT GAA GAT GCC CTC AGA AAC CAA CCC CTG           1035

GGC CCT GTG TTG AGC AAA GCT GCG TCT GTG GAG TGT ATC AGC CCC           1080

GTT ACA CCC AGA GCC CCG GAC GCC AAG ATG CTG GAG GAG CTT AAT           1125
```

```
GCT GAG CCC TGG TAC CAA GGC GAG ATG AGC AGG AAG GAG GCA GAG                1170

GCT CTA CTA CAG GAA GAT GGA GAC TTC CTA GTC AGG AAG AGT ACC                1215

ACC AAC CCC GGC TCC TTT GTC CTC ACA GGC ATG CAC AAT GGC CAG                1260

GCC AAG CAC CTG CTG CTG GTG GAC CCG GAA GGC ACG GTC CGG ACG                1305

AAG GAC AGG GTC TTT GAC AGC ATC AGT CAC CTC ATT ACT TAC CAC                1350

CTG GAG AGC AGC CTG CCC ATT GTC TCT GCC GGG AGT GAG CTT TGT                1395

CTC CGG CAA CCA GTG GAG AGG AAA CCC TGA                                    1425
```

(2) INFORMATION FOR SEQ ID NO:11:

(i) SEQUENCE CHARACTERISTICS:
        (A) LENGTH:474 amino acids
        (B) TYPE:amino acid
        (D) TOPOLOGY:linear (ii) MOLECULE TYPE:peptide (xi) SEQUENCE DESCRIPTION:SEQ ID NO:11:

```
Met Ser Ala Thr Arg Lys Ser Arg Ala Ser Asp Glu Pro Leu Pro
                  5                  10                  15

Arg Pro Pro Arg Gly Ala Pro His Ala Ser Asp Gln Val Leu Gly
             20                  25                  30

Ser Gly Val Thr Tyr Val Val Lys Tyr Leu Gly Cys Ile Glu Val
             35                  40                  45

Leu Arg Ser Met Arg Ser Leu Asp Phe Ser Thr Arg Thr Gln Val
             50                  55                  60

Thr Arg Glu Ala Ile Ser Arg Val Cys Glu Ala Val Pro Gly Ala
             65                  70                  75

Lys Gly Ala Phe Lys Lys Arg Lys Pro Pro Ser Lys Met Leu Ser
             80                  85                  90

Ser Ile Leu Gly Lys Ser Asn Leu Gln Phe Ala Gly Met Ser Ile
             95                 100                 105

Ser Leu Thr Ile Ser Thr Ala Ser Leu Asn Leu Arg Thr Pro Asp
            110                 115                 120

Ser Lys Gln Ile Ile Ser Asn His His Met Arg Ser Ile Ser Phe
            125                 130                 135

Ala Ser Gly Gly Asp Pro Asp Thr Thr Asp Tyr Val Ala Tyr Val
            140                 145                 150

Ala Lys Asp Pro Val Asn Arg Arg Ala Cys His Ile Leu Glu Cys
            155                 160                 165

Cys Asp Gly Leu Ala Gln Asp Val Ile Gly Ser Ile Gly Gln Ala
            170                 175                 180

Phe Glu Leu Arg Phe Lys Gln Tyr Leu Gln Cys Pro Ser Lys Ile
            185                 190                 195

Pro Ala Leu Gln Asp Arg Met Gln Ser Leu Asp Glu Pro Trp Thr
            200                 205                 210

Glu Glu Glu Gly Asp Gly Pro Asp His Pro Tyr Tyr Asn Ser Val
            215                 220                 225

Pro Asn Lys Met Pro Pro Gly Gly Phe Leu Asp Ala Arg Leu
            230                 235                 240

Lys Ala Arg Pro His Ala Pro Asp Ala Ala Gln Phe Ser Gly Lys
            245                 250                 255

Glu Gln Thr Tyr Tyr Gln Gly Arg His Leu Gly Asp Ala Phe Gly
            260                 265                 270
```

```
Glu Asp Trp Gln Arg Ala Pro Thr Arg Gln Gly Ser Leu Asp Ile
            275                 280                 285

Tyr Ser Thr Pro Glu Gly Lys Ala His Met Val Pro Val Gly Glu
            290                 295                 300

Thr Pro Thr Tyr Val Asn Thr Gln Pro Val Pro Gln Val Trp
            305                 310                 315

Pro Ala Ala Thr Ser Ser Thr Glu Ser Ser Pro Arg Lys Asp Leu
            320                 325                 330

Phe Asp Met Lys Pro Phe Glu Asp Ala Leu Arg Asn Gln Pro Leu
            335                 340                 345

Gly Pro Val Leu Ser Lys Ala Ala Ser Val Glu Cys Ile Ser Pro
            350                 355                 360

Val Thr Pro Arg Ala Pro Asp Ala Lys Met Leu Glu Glu Leu Asn
            365                 370                 375

Ala Glu Pro Trp Tyr Gln Gly Glu Met Ser Arg Lys Glu Ala Glu
            380                 385                 390

Ala Leu Leu Gln Glu Asp Gly Asp Phe Leu Val Arg Lys Ser Thr
            395                 400                 405

Thr Asn Pro Gly Ser Phe Val Leu Thr Gly Met His Asn Gly Gln
            410                 415                 420

Ala Lys His Leu Leu Leu Val Asp Pro Glu Gly Thr Val Arg Thr
            425                 430                 435

Lys Asp Arg Val Phe Asp Ser Ile Ser His Leu Ile Thr Tyr His
            440                 445                 450

Leu Glu Ser Ser Leu Pro Ile Val Ser Ala Gly Ser Glu Leu Cys
            455                 460                 465

Leu Arg Gln Pro Val Glu Arg Lys Pro
            470
```

(2) INFORMATION FOR SEQ ID NO:12:

(i) SEQUENCE CHARACTERISTICS:
        (A) LENGTH:492 base pairs
        (B) TYPE:nucleic acid
        (C) STRANDEDNESS:double strand
        (D) TOPOLOGY:linear (ii) MOLECULE TYPE:cDNA to mRNA (xi) SEQUENCE DESCRIPTION:SEQ ID NO:12:

```
CTG GGG TCG GGA GTC ACC TAT GTG GTC AAG TAC TTG GGA TGC ATC        45

GAA GTT CTG CGC TCA ATG AGG TCT CTT GAC TTC AGT ACA AGA ACT        90

CAG GTT ACC AGG GAA GCC ATC AGC CGT GTC TGC GAA GCT GTG CCA        135

GGC GCC AAA GGA GCC TTC AAG AAG AGA AAG CCT CCG AGT AAA ATG        180

CTG TCC AGC ATC CTG GGG AAG AGC AAC CTC CAG TTC GCA GGG ATG        225

AGC ATC TCC CTG ACC ATC TCC ACC GCC AGC CTG AAC CTG CGC ACT        270

CCT GAC TCC AAA CAG ATC ATA TCG AAC CAT CAC ATG CGG TCC ATC        315

TCC TTC GCC TCA GGG GGA GAC CCG GAC ACA ACA GAC TAT GTT GCC        360

TAC GTC GCT AAG GAC CCT GTG AAT CGC AGA GCT TGC CAC ATT CTG        405

GAA TGC TGT GAC GGG CTA GCC CAA GAT GTC ATC GGC TCC ATC GGA        450

CAA GCC TTT GAA CTC CGG TTC AAG CAG TAT TTG CAG TGT CCT             492
```

(2) INFORMATION FOR SEQ ID NO:13:

(i) SEQUENCE CHARACTERISTICS:
    (A) LENGTH:164 amino acids
    (B) TYPE:amino acid
    (D) TOPOLOGY:linear (ii) MOLECULE TYPE:peptide (xi) SEQUENCE DESCRIPTION:SEQ ID NO:13:

Leu Gly Ser Gly Val Thr Tyr Val Val Lys Tyr Leu Gly Cys Ile
                 5                  10                  15

Glu Val Leu Arg Ser Met Arg Ser Leu Asp Phe Ser Thr Arg Thr
                20                  25                  30

Gln Val Thr Arg Glu Ala Ile Ser Arg Val Cys Glu Ala Val Pro
                35                  40                  45

Gly Ala Lys Gly Ala Phe Lys Lys Arg Lys Pro Ser Lys Met
                50                  55                  60

Leu Ser Ser Ile Leu Gly Lys Ser Asn Leu Gln Phe Ala Gly Met
                65                  70                  75

Ser Ile Ser Leu Thr Ile Ser Thr Ala Ser Leu Asn Leu Arg Thr
                80                  85                  90

Pro Asp Ser Lys Gln Ile Ile Ser Asn His His Met Arg Ser Ile
                95                 100                 105

Ser Phe Ala Ser Gly Gly Asp Pro Asp Thr Thr Asp Tyr Val Ala
               110                 115                 120

Tyr Val Ala Lys Asp Pro Val Asn Arg Arg Ala Cys His Ile Leu
               125                 130                 135

Glu Cys Cys Asp Gly Leu Ala Gln Asp Val Ile Gly Ser Ile Gly
               140                 145                 150

Gln Ala Phe Glu Leu Arg Phe Lys Gln Tyr Leu Gln Cys Pro
               155                 160

(2) INFORMATION FOR SEQ ID NO:14:

(i) SEQUENCE CHARACTERISTICS:
        (A) LENGTH:288 base pairs
        (B) TYPE:nucleic acid
        (C) STRANDEDNESS:double strand
        (D) TOPOLOGY:linear (ii) MOLECULE TYPE:cDNA to mRNA (xi) SEQUENCE DESCRIPTION:SEQ ID NO:14:

TGG TAC CAA GGC GAG ATG AGC AGG AAG GAG GCA GAG GCT CTA CTA        45

CAG GAA GAT GGA GAC TTC CTA GTC AGG AAG AGT ACC ACC AAC CCC        90

GGC TCC TTT GTC CTC ACA GGC ATG CAC AAT GGC CAG GCC AAG CAC       135

CTG CTG CTG GTG GAC CCG GAA GGC ACG TCC GGA ACG AAG GAC AGG       180

GTC TTT GAC AGC ATC AGT CAC CTC ATT ACT TAC CAC CTG GAG AGC       225

AGC CTG CCC ATT GTC TCT GCC GGG AGT GAG CTT TGT CTC CGG CAA       270

CCA GTG GAG AGG AAA CCC                                           288

(2) INFORMATION FOR SEQ ID NO:15:

(i) SEQUENCE CHARACTERISTICS:
        (A) LENGTH:96 amino acids
        (B) TYPE:amino acid
        (D) TOPOLOGY:linear (ii) MOLECULE TYPE:peptide (xi) SEQUENCE DESCRIPTION:SEQ ID NO:15:

```
Trp Tyr Gln Gly Glu Met Ser Arg Lys Glu Ala Glu Ala Leu Leu
              5                  10                  15
Gln Glu Asp Gly Asp Phe Leu Val Arg Lys Ser Thr Thr Asn Pro
             20                  25                  30
Gly Ser Phe Val Leu Thr Gly Met His Asn Gly Gln Ala Lys His
             35                  40                  45
Leu Leu Leu Val Asp Pro Glu Gly Thr Val Arg Thr Lys Asp Arg
             50                  55                  60
Val Phe Asp Ser Ile Ser His Leu Ile Thr Tyr His Leu Glu Ser
             65                  70                  75
Ser Leu Pro Ile Val Ser Ala Gly Ser Glu Leu Cys Leu Arg Gln
             80                  85                  90
Pro Val Glu Arg Lys Pro
             95
```

(2) INFORMATION FOR SEQ ID NO:16:

(i) SEQUENCE CHARACTERISTICS:
        (A) LENGTH:1785 base pairs
        (B) TYPE:nucleic acid
        (C) STRANDEDNESS:double strand
        (D) TOPOLOGY:linear (ii) MOLECULE TYPE:cDNA to mRNA (xi) SEQUENCE DESCRIPTION:SEQ ID NO:16:

```
ATG CTT CCA CGC ACC AAG TAC AAC CGC TTC AGG AAT GAC TCG GTG      45
ACA TCG GTC GAT GAC CTT CTC CAC AGC CTG TCG GTG AGC GGC AGC      90
GGC GGC AAG GTC TCG GCG GAG CCC GCG GCG AGC CCC TAC CTG GTG     135
TCG GGC GAG GCG CTG CGC AAG GCG CCG GAC GAT GGG CCC GGC AGC     180
CTG GGC CAC CTG CTC CAC AAG GTG TCC CAC TTG AAA CTC TCC AGC     225
TCC GGC CTG CGT GGC CTG TCG TCG GCC GCC CGG GAG CGG GCA GGA     270
GCG CGG CTC TCG GGC AGC TGC AGC GCG CCC AGC CTG GCG GCC CCG     315
GAC GGT GGC AGC GCG ACC CCC GGG TCC CGT GCC CCG GCC GCC AGC     360
ATG AGC GCC ACC AGG AAG AGC CGG GCC AGC GAC GAG CCG TTG CCC     405
AGG CCC CCG CGG GGC GCG CCG CAC GCC AGC GAC CAG GTG CTG GGG     450
TCG GGA GTC ACC TAT GTG GTC AAG TAC TTG GGA TGC ATC GAA GTT     495
CTG CGC TCA ATG AGG TCT CTT GAC TTC AGT ACA AGA ACT CAG GTT     540
ACC AGG GAA GCC ATC AGC CGT GTC TGC GAA GCT GTG CCA GGC GCC     585
AAA GGA GCC TTC AAG AAG AGA AAG CCT CCG AGT AAA ATG CTG TCC     630
AGC ATC CTG GGG AAG AGC AAC CTC CAG TTC GCA GGG ATG AGC ATC     675
TCC CTG ACC ATC TCC ACC GCC AGC CTG AAC CTG CGC ACT CCT GAC     720
TCC AAA CAG ATC ATA TCG AAC CAT CAC ATG CGG TCC ATC TCC TTC     765
GCC TCA GGG GGA GAC CCG GAC ACA ACA GAC TAT GTT GCC TAC GTC     810
GCT AAG GAC CCT GTG AAT CGC AGA GCT TGC CAC ATT CTG GAA TGC     855
TGT GAC GGG CTA GCC CAA GAT GTC ATC GGC TCC ATC GGA CAA GCC     900
TTT GAA CTC CGG TTC AAG CAG TAT TTG CAG TGT CCT TCC AAG ATT     945
CCT GCT CTC CAG GAC CGA ATG CAG AGT CTG GAC GAG CCG TGG ACT     990
```

```
GAA GAA GAG GGA GAT GGC CCC GAT CAC CCG TAC TAC AAC AGC GTT       1035

CCC AAC AAG ATG CCT CCT CCA GGA GGG TTT CTC GAT GCT CGA TTG       1080

AAA GCC AGA CCC CAC GCA CCT GAT GCA GCC CAG TTT TCA GGA AAA       1125

GAG CAA ACT TAT TAC CAG GGA AGA CAC TTA GGA GAT GCA TTC GGT       1170

GAA GAC TGG CAG AGA GCA CCC ACC AGG CAA GGC TCC TTG GAC ATC       1215

TAT AGC ACA CCA GAA GGG AAA GCT CAC ATG GTT CCT GTA GGA GAA       1260

ACA CCA ACC TAT GTC AAC ACC CAG CCA GTC CCA CCA CAG GTT TGG       1305

CCA GCA GCA ACC AGC AGC ACT GAG AGC AGC CCA CGG AAG GAC CTC       1350

TTT GAC ATG AAG CCT TTT GAA GAT GCC CTC AGA AAC CAA CCC CTG       1395

GGC CCT GTG TTG AGC AAA GCT GCG TCT GTG GAG TGT ATC AGC CCC       1440

GTT ACA CCC AGA GCC CCG GAC GCC AAG ATG CTG GAG GAG CTT AAT       1485

GCT GAG CCC TGG TAC CAA GGC GAG ATG AGC AGG AAG GAG GCA GAG       1530

GCT CTA CTA CAG GAA GAT GGA GAC TTC CTA GTC AGG AAG AGT ACC       1575

ACC AAC CCC GGC TCC TTT GTC CTC ACA GGC ATG CAC AAT GGC CAG       1620

GCC AAG CAC CTG CTG CTG GTG GAC CCG GAA GGC ACG GTC CGG ACG       1665

AAG GAC AGG GTC TTT GAC AGC ATC AGT CAC CTC ATT ACT TAC CAC       1710

CTG GAG AGC AGC CTG CCC ATT GTC TCT GCC GGG AGT GAG CTT TGT       1755

CTC CGG CAA CCA GTG GAG AGG AAA CCC TGA                           1785
```

(2) INFORMATION FOR SEQ ID NO:17:

(i) SEQUENCE CHARACTERISTICS:
        (A) LENGTH:594 amino acids
        (B) TYPE:amino acid
        (D) TOPOLOGY:linear (ii) MOLECULE TYPE:peptide (xi) SEQUENCE DESCRIPTION:SEQ ID NO:17:

```
Met Leu Pro Arg Thr Lys Tyr Asn Arg Phe Arg Asn Asp Ser Val
              5                  10                  15

Thr Ser Val Asp Asp Leu Leu His Ser Leu Ser Val Ser Gly Ser
             20                  25                  30

Gly Gly Lys Val Ser Ala Glu Pro Ala Ala Ser Pro Tyr Leu Val
             35                  40                  45

Ser Gly Glu Ala Leu Arg Lys Ala Pro Asp Asp Gly Pro Gly Ser
             50                  55                  60

Leu Gly His Leu Leu His Lys Val Ser His Leu Lys Leu Ser Ser
             65                  70                  75

Ser Gly Leu Arg Gly Leu Ser Ser Ala Ala Arg Glu Arg Ala Gly
             80                  85                  90

Ala Arg Leu Ser Gly Ser Cys Ser Ala Pro Ser Leu Ala Ala Pro
             95                 100                 105

Asp Gly Gly Ser Ala Thr Pro Gly Ser Arg Ala Pro Ala Ala Ser
            110                 115                 120

Met Ser Ala Thr Arg Lys Ser Arg Ala Ser Asp Glu Pro Leu Pro
            125                 130                 135

Arg Pro Pro Arg Gly Ala Pro His Ala Ser Asp Gln Val Leu Gly
            140                 145                 150

Ser Gly Val Thr Tyr Val Val Lys Tyr Leu Gly Cys Ile Glu Val
            155                 160                 165
```

```
Leu Arg Ser Met Arg Ser Leu Asp Phe Ser Thr Arg Thr Gln Val
            170                 175                 180

Thr Arg Glu Ala Ile Ser Arg Val Cys Glu Ala Val Pro Gly Ala
            185                 190                 195

Lys Gly Ala Phe Lys Lys Arg Lys Pro Pro Ser Lys Met Leu Ser
            200                 205                 210

Ser Ile Leu Gly Lys Ser Asn Leu Gln Phe Ala Gly Met Ser Ile
            215                 220                 225

Ser Leu Thr Ile Ser Thr Ala Ser Leu Asn Leu Arg Thr Pro Asp
            230                 235                 240

Ser Lys Gln Ile Ile Ser Asn His His Met Arg Ser Ile Ser Phe
            245                 250                 255

Ala Ser Gly Gly Asp Pro Asp Thr Thr Asp Tyr Val Ala Tyr Val
            260                 265                 270

Ala Lys Asp Pro Val Asn Arg Arg Ala Cys His Ile Leu Glu Cys
            275                 280                 285

Cys Asp Gly Leu Ala Gln Asp Val Ile Gly Ser Ile Gly Gln Ala
            290                 295                 300

Phe Glu Leu Arg Phe Lys Gln Tyr Leu Gln Cys Pro Ser Lys Ile
            305                 310                 315

Pro Ala Leu Gln Asp Arg Met Gln Ser Leu Asp Glu Pro Trp Thr
            320                 325                 330

Glu Glu Glu Gly Asp Gly Pro Asp His Pro Tyr Tyr Asn Ser Val
            335                 340                 345

Pro Asn Lys Met Pro Pro Pro Gly Gly Phe Leu Asp Ala Arg Leu
            350                 355                 360

Lys Ala Arg Pro His Ala Pro Asp Ala Ala Gln Phe Ser Gly Lys
            365                 370                 375

Glu Gln Thr Tyr Tyr Gln Gly Arg His Leu Gly Asp Ala Phe Gly
            380                 385                 390

Glu Asp Trp Gln Arg Ala Pro Thr Arg Gln Gly Ser Leu Asp Ile
            395                 400                 405

Tyr Ser Thr Pro Glu Gly Lys Ala His Met Val Pro Val Gly Glu
            410                 415                 420

Thr Pro Thr Tyr Val Asn Thr Gln Pro Val Pro Pro Gln Val Trp
            425                 430                 435

Pro Ala Ala Thr Ser Ser Thr Glu Ser Ser Pro Arg Lys Asp Leu
            440                 445                 450

Phe Asp Met Lys Pro Phe Glu Asp Ala Leu Arg Asn Gln Pro Leu
            455                 460                 465

Gly Pro Val Leu Ser Lys Ala Ala Ser Val Glu Cys Ile Ser Pro
            470                 475                 480

Val Thr Pro Arg Ala Pro Asp Ala Lys Met Leu Glu Glu Leu Asn
            485                 490                 495

Ala Glu Pro Trp Tyr Gln Gly Glu Met Ser Arg Lys Glu Ala Glu
            500                 505                 510

Ala Leu Leu Gln Glu Asp Gly Asp Phe Leu Val Arg Lys Ser Thr
            515                 520                 525

Thr Asn Pro Gly Ser Phe Val Leu Thr Gly Met His Asn Gly Gln
            530                 535                 540

Ala Lys His Leu Leu Leu Val Asp Pro Glu Gly Thr Val Arg Thr
            545                 550                 555

Lys Asp Arg Val Phe Asp Ser Ile Ser His Leu Ile Thr Tyr His
```

```
              560                 565                 570
Leu Glu Ser Ser Leu Pro Ile Val Ser Ala Gly Ser Glu Leu Cys
            575                 580                 585
Leu Arg Gln Pro Val Glu Arg Lys Pro
            590
```

(2) INFORMATION FOR SEQ ID NO:18:

(i) SEQUENCE CHARACTERISTICS:
        (A) LENGTH:16 amino acids
        (B) TYPE:amino acid
        (D) TOPOLOGY:linear (ii) MOLECULE TYPE:peptide (xi) SEQUENCE DESCRIPTION:SEQ ID NO:18:

```
Pro Trp Thr Glu Glu Glu Gly Asp Gly Ser Asp His Pro Tyr Tyr Asn
              5                  10                  15
```

(2) INFORMATION FOR SEQ ID NO:19:

(i) SEQUENCE CHARACTERISTICS:
        (A) LENGTH:15 amino acids
        (B) TYPE:amino acid
        (D) TOPOLOGY:linear (ii) MOLECULE TYPE:peptide (xi) SEQUENCE DESCRIPTION:SEQ ID NO:19:

```
Gln Thr Pro Leu Arg Gln Gly Ser Ser Asp Ile Tyr Ser Thr Pro
              5                  10                  15
```

(2) INFORMATION FOR SEQ ID NO:20:

(i) SEQUENCE CHARACTERISTICS:
        (A) LENGTH:11 amino acids
        (B) TYPE:amino acid
        (D) TOPOLOGY:linear (ii) MOLECULE TYPE:peptide (xi) SEQUENCE DESCRIPTION:SEQ ID NO:20:

```
Met Ala Ser Met Thr Gly Gly Gln Gln Met Gly
              5                  10
```

(2) INFORMATION FOR SEQ ID NO:21:

(i) SEQUENCE CHARACTERISTICS:
        (A) LENGTH:260 amino acids
        (B) TYPE:amino acid
        (D) TOPOLOGY:linear (ii) MOLECULE TYPE:peptide (xi) SEQUENCE DESCRIPTION:SEQ ID NO:21:

```
Leu Gly Pro Gly Val Thr Tyr Val Val Lys Tyr Leu Gly Cys Ile
              5                  10                  15
Glu Val Leu Arg Ser Met Arg Ser Leu Asp Phe Ser Thr Arg Thr
            20                  25                  30
Gln Ile Thr Arg Glu Ala Ile Ser Arg Val Cys Glu Ala Val Pro
            35                  40                  45
Gly Ala Lys Gly Ala Phe Lys Lys Arg Lys Pro Pro Ser Lys Met
            50                  55                  60
Leu Ser Ser Ile Leu Gly Lys Ser Asn Leu Gln Phe Ala Gly Met
            65                  70                  75
```

```
Ser Ile Ser Leu Thr Ile Ser Thr Ala Ser Leu Asn Leu Arg Thr
             80                  85                  90

Pro Asp Ser Lys Gln Ile Ile Ala Asn His His Met Arg Ser Ile
             95                 100                 105

Ser Phe Ala Ser Gly Gly Asp Pro Asp Thr Thr Asp Tyr Val Ala
            110                 115                 120

Tyr Val Ala Lys Asp Pro Val Asn Arg Arg Ala Cys His Ile Leu
            125                 130                 135

Glu Cys Cys Asp Gly Leu Ala Gln Asp Val Ile Gly Ser Ile Gly
            140                 145                 150

Gln Ala Phe Glu Leu Arg Phe Lys Gln Tyr Leu Gln Cys Pro Trp
            155                 160                 165

Tyr Gln Gly Glu Met Ser Arg Lys Glu Ala Glu Gly Leu Leu Glu
            170                 175                 180

Lys Asp Gly Asp Phe Leu Val Arg Lys Ser Thr Thr Asn Pro Gly
            185                 190                 195

Ser Phe Val Leu Thr Gly Met His Asn Gly Gln Ala Lys His Leu
            200                 205                 210

Leu Leu Val Asp Pro Glu Gly Thr Ile Arg Thr Lys Asp Arg Val
            215                 220                 225

Phe Asp Ser Ile Ser His Leu Ile Asn His His Leu Glu Ser Ser
            230                 235                 240

Leu Pro Ile Val Ser Ala Gly Ser Glu Leu Cys Leu Gln Gln Pro
            245                 250                 255

Val Glu Arg Lys Gln
            260

(2) INFORMATION FOR SEQ ID NO:22:

(i) SEQUENCE CHARACTERISTICS:
        (A) LENGTH:260 amino acids
        (B) TYPE:amino acid
        (D) TOPOLOGY:linear (ii) MOLECULE TYPE:peptide (xi) SEQUENCE DESCRIPTION:SEQ ID NO:22:

Leu Gly Ser Gly Val Thr Tyr Val Val Lys Tyr Leu Gly Cys Ile
              5                  10                  15

Glu Val Leu Arg Ser Met Arg Ser Leu Asp Phe Ser Thr Arg Thr
             20                  25                  30

Gln Val Thr Arg Glu Ala Ile Ser Arg Val Cys Glu Ala Val Pro
             35                  40                  45

Gly Ala Lys Gly Ala Phe Lys Lys Arg Lys Pro Pro Ser Lys Met
             50                  55                  60

Leu Ser Ser Ile Leu Gly Lys Ser Asn Leu Gln Phe Ala Gly Met
             65                  70                  75

Ser Ile Ser Leu Thr Ile Ser Thr Ala Ser Leu Asn Leu Arg Thr
             80                  85                  90

Pro Asp Ser Lys Gln Ile Ile Ser Asn His His Met Arg Ser Ile
             95                 100                 105

Ser Phe Ala Ser Gly Gly Asp Pro Asp Thr Thr Asp Tyr Val Ala
            110                 115                 120

Tyr Val Ala Lys Asp Pro Val Asn Arg Arg Ala Cys His Ile Leu
            125                 130                 135

Glu Cys Cys Asp Gly Leu Ala Gln Asp Val Ile Gly Ser Ile Gly
            140                 145                 150
```

```
Gln Ala Phe Glu Leu Arg Phe Lys Gln Tyr Leu Gln Cys Pro Trp
                155             160             165

Tyr Gln Gly Glu Met Ser Arg Lys Glu Ala Glu Ala Leu Leu Gln
                170             175             180

Glu Asp Gly Asp Phe Leu Val Arg Lys Ser Thr Thr Asn Pro Gly
                185             190             195

Ser Phe Val Leu Thr Gly Met His Asn Gly Gln Ala Lys His Leu
                200             205             210

Leu Leu Val Asp Pro Glu Gly Thr Val Arg Thr Lys Asp Arg Val
                215             220             225

Phe Asp Ser Ile Ser His Leu Ile Thr Tyr His Leu Glu Ser Ser
                230             235             240

Leu Pro Ile Val Ser Ala Gly Ser Glu Leu Cys Leu Arg Gln Pro
                245             250             255

Val Glu Arg Lys Pro
                260
```

BRAIN-SPECIFIC ADAPTER MOLECULE, GENE THEREOF, AND ANTIBODY THERETO

BACKGROUND OF THE INVENTION

1. Field of the Invention

This invention relates to a novel brain-specific adapter molecule, its gene, and antibodies to it.

2. Related Background Art

Nerve growth factor (NGF) is known to mainly stimulate the survival and growth of neurons of the brain and maintain the neuronal network through these activities. Neurons of the Meynert's basal ganglia, for example, integrate information from the lower regions of the cerebrum, and constantly send control signals to the cerebral cortex. These neurons receive NGF biosynthesized by neurons of the cerebral cortex, and sustain their survival (Thoenen, Trend NeuroSci., 14, 165–170, 1991, or Hatanaka, H., Cell Engineering, 9, 866–876, 1990).

Based on these findings, NGF is considered to have a high possibility for clinical use in the treatment of various neurological diseases, including recessive ones (e.g., dementia of the Alzheimer type and Parkinson's disease). Orthon et al. (J. Neural Transm. Park. Dement. Sect., 4, 79–95, 1992) have reported clinical use of NGF in patients with Alzheimer's dementia.

NGF actually transmits necessary signals into cells through NGF receptors, and studies of the pathways for the signals are under way (for example, Heumann, Current opinion in Neurobiology, 4, 668–679, 1994). Findings to be obtained through these studies are expected to serve for the direct clinical use of NGF in treating neurological diseases. In the diagnosis and treatment of cancer which abnormalities in growth factors similarly take a great part in, the achievements of researches on the signaling pathways of growth factors have reached the level of clinical application (Nikkei Biotechnology, 8–28, 2, 1995).

SUMMARY OF THE INVENTION

An object of the present invention is to search for and isolate a novel factor involved in the signaling pathways in neurons of the brain (e.g., the signaling pathways within the neurons NGF acts on).

Another object of the invention is to provide means of measuring tyrosine kinase activity in a cell or tissue by use of the novel factor (FC99 protein), the gene (FC99 gene) encoding it, and antibodies to it claimed in the invention.

The present invention will be more fully understood from the detailed description given hereinbelow and the accompanying drawings, which are given by way of illustration only and are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will be apparent to those skilled in the art from this detailed description.

BRIEF DESCRIPTION OF THE DRAWINGS

FIG. 1 is a view showing a comparison of the amino acid sequences of FC99 and Shc in the PTB domain (uppper side A) and the SH2 domain (bottom side B), in which the numeral on the right of the row denotes how many residues in FC99 and Shc are present until the amino acid reside located at the end of the row. For FC99, the numeral shows the position in the amino acid sequence described as Seq. ID No. 1 in the Sequence Listing;

DESCRIPTION OF THE PREFERRED EMBODIMENTS

We have conducted extensive studies to attain the aforementioned objects, and found that these objects can be attained by screening from a normalized cDNA library using human cerebrum-derived mRNA (prepared in accordance with the method of Sasaki et al., DNA Research 1, 91–96, 1994). This article is hereby incorporated by reference.

That is, we have succeeded in isolating a gene (hereinafter referred to as FC99 gene or N-Shc gene) encoding a polypeptide having two specific domains (PTB domain as in van derGeer et al., Trends Biol. Sci., 20, 277–280, 1995, and SH2 domain as in Pawson, Nature, 373, 573–580, 1995) which are known to recognize phosphorylated tyrosine (its biochemical mechanisms are described, for example, in Heumann: Current opinion in Neurobiology, 4, 668–679, 1994, or Pawson: Nature, 373, 573–580, 1995) known to work as a signal molecule in the signaling pathways in neurons of the brain (e.g., the signaling pathways in neurons where NGF acts).

Figure 2:
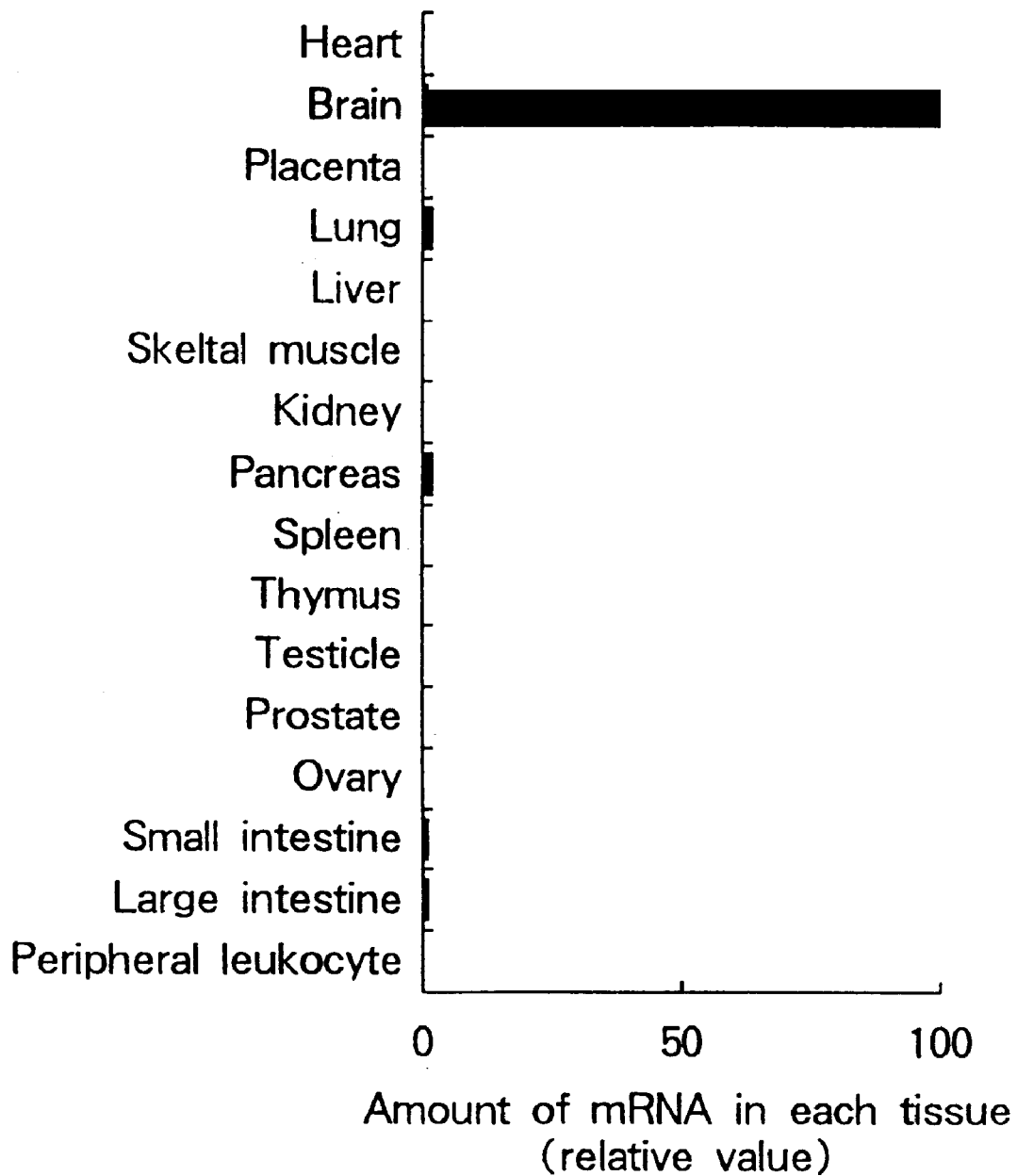
FIG. 2 is a chart showing the amounts of FC99 mRNA expressed in 16 kinds of tissues, with the amount of the mRNA in the brain being designated as 100, and those in the other tissues being relative amounts to it.

We have also clarified that the expression of the FC99 gene is specific for the brain among the 16 tissues investigated (see FIG. 2).

We have further made it clear that the sequence of the resulting FC99 is very similar to Shc (Pelicci et al., Cell, 70, 93–104, 1992), known as an adapter molecule in intracellular signaling pathways, in terms of the amino acid sequences of the PTB domain and the SH2 domain (see FIG. 1).

A comparison of the FC99 obtained in the present invention with the Shc has shown that a tyrosine residue which undergoes phosphorylation (Shc has been shown to bind Grb2, another adapter molecule, via this phosphorylated tyrosine; van der Geer et al., Current Biology, 5, 404–412, 1995), indispensable for Shc to act as an adapter molecule in the intracellular signaling pathways, is preserved in FC99.

As described above, the FC99 protein identified in the present invention is presumed to function as an adapter molecule in phosphorylated tyrosine-mediated intracellular signaling pathways. Thus, the FC99 protein obtained in the present invention and its genetic information can be applied as tools for study of the intracellular signaling pathways, as therapeutic methods or agents for diseases involving abnormalities in the intracellular signaling pathways, and as testing methods or diagnostic reagents for the diseases.

More particularly, the invention relates to polypeptide (1) containing in the molecule at least an amino acid sequence described as Seq. ID No. 1 in the Sequence Listing.

The invention also relates to polynucleotide (2) containing in the molecule at least a base sequence described as Seq. ID No. 2 in the Sequence Listing.

The invention also relates to polypeptide (3) containing in the molecule at least an amino acid sequence described as Seq. ID No. 7 in the Sequence Listing.

The invention also relates to polynucleotide (4) containing in the molecule at least a base sequence described as Seq. ID No. 8 in the Sequence Listing.

The invention also relates to polypeptide (5) containing in the molecule at least an amino acid sequence described as Seq. ID No. 3 in the Sequence Listing.

The invention also relates to polynucleotide (6) containing in the molecule at least a base sequence described as Seq. ID No. 4 in the Sequence Listing.

The invention also relates to polypeptide (7) containing in the molecule at least an amino acid sequence described as Seq. ID No. 5 in the Sequence Listing.

The invention also relates to polynucleotide (8) containing in the molecule at least a base sequence described as Seq. ID No. 6 in the Sequence Listing.

The invention also relates to polypeptide (9) containing in the molecule at least both of an amino acid sequence described as Seq. ID No. 3 in the Sequence Listing and an amino acid sequence described as Seq. ID No. 5 in the Sequence Listing.

The invention also relates to polynucleotide (10) containing in the molecule at least both of a base sequence described as Seq. ID No. 4 in the Sequence Listing and a base sequence described as Seq. ID No. 6 in the Sequence Listing.

The invention also relates to polypeptide (11) containing the amino acid sequence of the polypeptide (1), (3), (5), (7) or (9) that has undergone spontaneous or induced mutation, and having the ability to bind a polypeptide containing a phosphorylated tyrosine residue.

The invention also relates to polynucleotide (12) encoding polypeptide (11).

The invention also relates to polynucleotide (13) having all or part of the sequence of the antisense strand of the polynucleotide (2), (4), (6), (8), (10) or (12), and inhibiting the biosynthesis of the polypeptide (1), (3), (5), (7), (9) or (11).

The invention also relates to polynucleotide (14) having all or part of the sequence of the antisense strand of the polynucleotide (2), (4), (6), (8), (10) or (12) that has undergone spontaneous or induced mutation, and inhibiting the biosynthesis of the polypeptide (1), (3), (5), (7), (9) or (11).

The invention also relates to polypeptide (15) containing in the molecule at least an amino acid sequence described as Seq. ID No. 11 in the Sequence Listing.

The invention also relates to polynucleotide (16) containing in the molecule at least a base sequence described as Seq. ID No. 10 in the Sequence Listing. The invention also relates to polypeptide (17) containing in the molecule at least an amino acid sequence described as Seq. ID No. 17 in the Sequence Listing.

The invention also relates to polynucleotide (18) containing in the molecule at least a base sequence described as Seq. ID No. 16 in the Sequence Listing.

The invention also relates to polypeptide (19) containing in the molecule at least an amino acid sequence described as Seq. ID No. 13 in the Sequence Listing.

The invention also relates to polynucleotide (20) containing in the molecule at least a base sequence described as Seq. ID No. 12 in the Sequence Listing.

The invention also relates to polypeptide (21) containing in the molecule at least an amino acid sequence described as Seq. ID No. 15 in the Sequence Listing.

The invention also relates to polynucleotide (22) containing in the molecule at least a base sequence described as Seq. ID No. 14 in the Sequence Listing.

The invention also relates to polypeptide (23) containing in the molecule at least the polypeptide of (19) or (21).

The invention also relates to polynucleotide (24) containing in the molecule at least the polynucleotide of (20) or (22).

The invention also relates to polypeptide (25) containing the amino acid sequence of the polypeptide (15), (17), (19), (21) or (23) that has undergone spontaneous or induced mutation, and having the ability to bind a polypeptide containing a phosphorylated tyrosine residue.

The invention also relates to polynucleotide (26) encoding the polypeptide (25).

The invention also relates to polynucleotide (27) having all or part of the sequence of the antisense strand of the polynucleotide (14), (18), (20), (22), (24) or (26), and inhibiting the biosynthesis of the polypeptide (15), (17), (19), (21), (23) or (25).

The invention also relates to polynucleotide (28) having all or part of the sequence of the antisense strand of the polynucleotide (16), (18), (20), (22), (24) or (26) that has undergone spontaneous or induced mutation, and inhibiting the biosynthesis of the polypeptide (15), (17), (19), (21), (23) or (25).

The invention also relates to a recombinant plasmid containing the polynucleotide (2), (4), (6), (8), (10), (12), (14), (18), (20), (22), (24) or (26).

The invention also relates to recombinant microorganism cells transformed with the above plasmid.

The invention also relates to an antibody to a polypeptide having the amino acid sequence of (1), (3), (5), (7), (15), (17), (19) or (21).

The invention also provides a method of separating a polypeptide having the amino acid sequence of (1), (3), (5), (7), (15), (17), (19) or (21) by use of the above antibody.

The invention also provides a method of measuring tyrosine kinase activity in a cell or tissue, which comprises separating polypeptide having the amino acid sequence of (1), (3), (5), (7), (15), (17), (19) or (21) by use of the above antibody, and detecting a phosphorylated tyrosine residue in the separated polypeptide.

Embodiments of the present invention will be described in detail below.

For the identification and isolation of a novel brain-specific adapter molecule concerned with the invention, cells derived from any regions of the brain may be used. They may be cells from the hippocampus or caudate nucleus. Cells from the human or rat cerebrum are used preferably.

To identify the novel brain-specific adapter molecule, various chemical structural properties or biological chemical properties that the novel brain-specific adapter molecule requires to function as a phosphorylated signaling control factor may be utilized, and used as markers for search. For this purpose, it is possible to utilize the properties that the novel brain-specific adapter molecule binds to phosphorylated tyrosine on a specific polypeptide (say, NGF receptor) known to act as a signal molecule in a signal transmission system from a cell membrane or within a cell. In the present invention, structural similarity to the chemical structure of, say, Shc molecule, known to act as an adapter molecule in the NGF signaling system may be used as a search marker for the novel brain-specific adapter molecule. With the Shc, there have been known some partial peptide structures that may be essential for activity as the adapter molecule of the NGF signaling system. The relations of these structures with the respective activities are also under investigation. Such structures include the PTB (phosphorylated tyrosine binding) domain, the Gbr2 binding site, and the SH2 domain. Thus, whether an amino acid sequence highly homologous to the amino acid sequence of any of these specific regions is included or not can be used as an evaluation criterion. As this method of evaluation, there can be used, although not limited to, various methods based on comparisons with known Shc amino acid sequences (for instance, evaluation of a significant difference by calculation of homology to these amino acid sequences).

The form of samples for search is not limited in the present invention. Methods are usable which enable polypeptides having the above-described properties to be identified and isolated from cells directly or indirectly in a suitable manner (e.g., screening of an expression library using antibodies to Shc or its partial peptide). Alternatively, a method of searching for and identifying a gene encoding the polypeptide from a suitable cDNA library (for instance, random sampling) can be used. In the present invention, it is particularly preferred that a group of cDNA's selected from a suitable cDNA library by random sampling is used as samples for search.

(Preparation of cDNA library)

For the selection of the above-mentioned suitable cDNA library, the present invention involves no limitations, and cDNA libraries available from various marketed products can be used. In the present invention, normalized cDNA library can be used particularly preferably. This is obtained, for example, by the method of Sasaki et al. (DNA Research 1, 91–96, 1994), and contains the uniform amounts of the respective cDNA's.

(Cloning of FC99 gene cDNA)

In the present invention, there is no restriction on the extent of screening of the resulting normalized human brain cDNA library. Part of this library can be selected by a suitable sampling method. In this invention, screening of about $1 \times 10^3$ to $5 \times 10^3$ clones is preferred.

The way of obtaining a plasmid during screening is not restricted, and may be an ordinary known method. An example of this method is to cut out the insert by digestion with a restriction enzyme, and incorporate it into a plasmid vector using a ligase (e.g., Cell Engineering Experiments Protocol, by Yamamoto et al., Shujunsha, 71–107, 1991); or is in vivo excision using a helper phage (e.g., the method described in Uni-ZAP XR Cloning Kit Instruction Manual, by Stratagene). In the invention, conversion into the form of a plasmid by in vivo excision using a helper phage is particularly preferred.

(Determination of base sequence)

By determining the base sequence of the insert of the so obtained plasmid, it becomes possible to select a plasmid containing a gene encoding an amino acid sequence highly complementary to the aforementioned two characteristic domains of the Shc. The invention imposes no restriction on whether to analyze part or whole of the insert. Preferably, it is also possible in the invention to determine a base sequence of a suitable length and select a more suitable plasmid based on the results. That is, it is preferred in the invention to determine several base sequences at the 51'-terminal, predict amino acid sequences encoded by the determined base sequences, and select a plasmid on the basis of the results. In this case, at least 200 bases are preferably analyzed for the insert at the 5'-terminal. This is necessary to evaluate homology to the aforesaid domains.

The way of determining the base sequence at the 5'-terminal of the selected plasmid (not restricted; for example, can be selected randomly in a suitable number) is not restricted in the invention, but may be a known method. For instance, a method relying on Taq cycle sequencing (Biotechniques, 7, 494–499, 1989) is usable particularly preferably.

The method of comparison with the known Shc on the basis of the amino acid sequence from the resulting base sequence is not restricted, but homology analysis by an ordinary method can be performed. For example, homology analysis becomes possible by use of a commercially available program (e.g., GENETYX program (Ver. 27, Software Development Co.)) and protein database (e.g., protein database (NBRF, Release 43)). This homology analysis permits the selection of, say, a sequence with 30% or higher homology in consecutive 100 residues to the sequence of the Shc.

For more detailed analysis of the plasmid selected in the above manner, screening is done for isolating a clone containing the whole of the region encoding the protein of interest. No restriction is imposed on the way of the screening. In the invention, the 5'-terminal base sequence information obtained above is used preferably. There is no restriction on whether all or some of the base sequences should be used. It is enough that screening can be carried out using these base sequences. For instance, about a half of the resulting base sequences may be utilized. This is dependent on the screening method to be used.

Various known methods can be used preferably, and without restriction, for screening. For example, hybridization using a labeled oligonucleotide, or RACE using a primer heading in the 5'-direction or 3'-direction is particularly preferred. In the invention, screening is preferably performed by hybridization using as a probe a labeled oligonucleotide having a PTB domain-encoding base sequence among the base sequences obtained above. There is no restriction on the labeling, $[\alpha-^{32}P]dCPT$ or digoxigenin can be used preferably. The conditions for hybridization are not restricted, and various known conditions are usable preferably (e.g., Cell Engineering Experiments Protocol, by Yamamoto et al., Shujunsha, 57–65, 1991).

The method of determining the base sequence of the insert from the positive clone screened in the above manner is not restricted, but various known methods can be used. An example is to produce deletion mutants, determine the base sequences of the respective clones, and join them together.

The above-described various known methods can be used to determine the base sequence of the longest insert of the inserts obtained above. An example is to prepare sequence primers successively from the portion having the base sequence determined, and read them.

(Determined FC99 base sequence)

A polynucleotide containing a base sequence encoding the determined human FC99 polypeptide is represented by Seq. ID No. 2 in the Sequence Listing or Seq. ID No. 8 in the Sequence Listing.

This polynucleotide related to the present invention includes a polynucleotide comprising a base sequence having no ATG linked to the 5'-terminal of Seq. ID No. 2 in the Sequence Listing or Seq. ID No. 8 in the Sequence Listing.

The polynucleotide of the invention also includes DNA containing 5'-flanking polynucleotide.

Also, part pf the structure of polynucleotide and the structure of a polypeptide deduced therefrom can be mutated spontaneously or artificially without changing the main activity (phosphorylated tyrosine binding capacity).

Thus, the polynucleotide of the invention also contains a base sequence encoding a polypeptide having a structure corresponding to a homologous isomer of the polypeptide of the invention.

Furthermore, at least one base of the base sequence of a polynucleotide can be replaced by another kind of base, without changing the amino acid sequence of a polypeptide produced from the polynucleotide, in accordance with the degeneracy of the genetic code. Thus, the polynucleotide of the invention can also contain a base sequence converted by substitution based on the degeneracy of the genetic code. For example, an amino acid sequence deduced from a base sequence obtained by such substitution performed for the base sequence of Seq. ID No. 2 in the Sequence Listing or Seq. ID No. 8 in the Sequence Listing agrees with the amino acid sequence of Seq. ID No. 1 in the Sequence Listing or Seq. ID No. 7 in the Sequence Listing, respectively.

(Amino acid sequence of FC99)

The amino acid sequence of FC99 is estimated from the polynucleotide determined by the foregoing method. The amino acid sequence of the FC99 polypeptide is described as Seq. ID No. 1 or 7 in the Sequence Listing.

The amino acid sequence relevant to the invention also includes a polypeptide having no methionine joined to the N-terminus of the amino acid sequence.

Also, part of the structure of the polynucleotide encoding a polypeptide can be varied by spontaneous or artificial mutation (e.g., Molecular Cloning, A Laboratory manual, 2nd ed., Cold Spring Harbor Laboratory Press, 15.1–15.113, 1989) without changing the main activity of the polypeptide. The polypeptide of FC99 related to the invention also includes a polypeptide having a structure corresponding to a homologous mutant of the polypeptide having the above-mentioned amino acid sequence.

(Characteristics as adapter molecule)

The amino acid sequence translated from the determined base sequence shows significant homology to the known human Shc as depicted in FIG. 1. Actually, the base sequence, and the amino acid sequence based thereon, of the PTB domains shown in Seq. ID. No. 4 of the Sequence Listing and Seq. ID. No. 3 of the Sequence Listing bear homology of 77.4% to human Shc (see FIG. 1 upper side A).

Homology to human Shc in the SH2 domain shown in Seq. ID. No. 6 and Seq. ID. No. 5 of the Sequence Listing is found to reach 67.7% (see FIG. 1 bottom side B).

Comparison of FC99 obtained in the invention with Shc has shown that the FC99 retains tyrosine residues which undergo phosphorylation (Shc has been shown to bind to Grb2, another adapter molecule, via this phosphorylated tyrosine (van der Geer et al., Current Biology, 5, 404–412, 1995)) indispensable for Shc to act as an adapter molecule in intracellular signaling pathways.

(FC99-containing transformed *E. coli*)

A suitable strain of Escherichia coli (*E. coli*) can be transformed with a clone containing the longest insert obtained above (e.g., Cell Engineering Experiments Protocol (Shujunsha, 1991), 105–107).

*E. coli* transformed in the above-described fashion with pBluescriptSK⁻, plasmid containing a polynucleotide having the base sequence described as Seq. ID No. 8 in the Sequence Listing was named pBS-FC99, and deposited on Oct. 11, 1995 at the National Institute of Bioscience and Human Technology (1–3, Higashi 1-chome, Tsukuba-shi, Ibaraki-ken 305 JAPAN), Agency of Industrial Science and Technology, Ministry of International Trade and Industry (accession number: FERM P-15228). This transformant was transferred to international deposition on Sep. 25 1996 (accession number: FERM BP-5671).

(Preparation of anti-FC99 antibody and detection of FC99 protein)

Antibodies can be prepared in accordance with the method described in "Antibodies: A Laboratory Manual" (Cold Spring Harbor Laboratory Press, 1988) using a part or whole of one of polypeptides consisiting of the amino acids described as Seq. ID Nos. 1, 7, 3, 5, 11, 17, 13 and 15 in the Sequence Listing, or using purified FC99 protein. The polypeptide used is desirably one having antigenicity and more than 8 amino acid residues long. To obtain antisera by immunizing the rabbit with the polypeptide, for instance, can be easily practiced by known means. If polyclonal antibody with adequate antibody titer is obtained by immunization as the results of Example 3 show, monoclonal antibody can be easily produced by a hybridoma with lymphocytes of an immunized animal (e.g., "Antibodies: A Laboratory Manual" (Cold Spring Harbor Laboratory Press, 1988)). Thus, production of monoclonal antibody in the invention is easy for those skilled in the art.

Using the so obtained antibody, FC99 can be identified and detected by western blotting. That is, a sample containing FC99 protein is flowed over polyacrylamide gel, and reacted with the above-described antibody, whereby a band corresponding to the FC99 protein can be detected. This method can be performed following a known method as described in "Antibodies: A Laboratory Manual" (Cold Spring Harbor Laboratory Press, 1988).

(Detection of activated tyrosine kinase using anti-FC99 antibody)

The Shc protein is known to be a good substrate for a wide variety of tyrosine kinases. According to Oncogene (1995), 11, pp. 899–907, for example, a high degree of phosphorylation of Shc is detected in almost all types of cancer where activation of tyrosine kinase takes part (about a two-digit difference from normal tissues is observed). Such types of cancer include types where a tyrosine kinase receptor such as EGF receptor is involved, and types where a cytoplasmic tyrosine kinase such as src is involved. Thus, tyrosine kinases are estimated to play some role in about a half of all types of cancer. Against those types of cancer which the activation of tyrosine kinase takes part in, an inhibitor of tyrosine kinase must be effective as an anti-cancer drug. Thus, the validity of this chemotherapy may be evaluated by measuring high phosphorylation of Shc.

This discussion may hold true of the FC99 protein which belongs to the same family as the Shc protein. In other words, it may be possible to separate the FC99 protein by use of anti-FC99 antibody, and detect the phosphorylation of the tyrosine residue of the separated FC99 protein. Actually, as described in detail in Example 5, immunoprecipitation is performed using an antibody which recognizes the FC99 protein, whereafter the precipitate is reacted with anti-phosphorylated tyrosine antibody. This experiment shows that the tyrosine residue of the FC99 protein is phosphorylated with activated EGF receptor. Thus, the FC99 protein is separated by immunoprecipitation using an FC99 protein-recognizing antibody or an equivalent method, and then the degree of phosphorylation of its tyrosine residue is investigated. This may be able to provide a method of screening for the presence of activated tyrosine kinase in a cell or tissue. Hence, as with the previous discussion on Shc, this method will open up a use of assessing the validity of chemotherapy for cancer.

(Isolation of rat FC99 gene, and its base sequence and amino acid sequence)

The ways of isolating rat-derived FC99 gene, determining the base sequence of the resulting gene, and determining an amino acid sequence on the basis of the results are substantially the same as those explained in detail in regard to the human FC99 gene. More details will be offered in Example 6 to follow.

As with the human FC99 gene, a polynucleotide having the whole or part of the determined base sequence encoding the rat FC99 polypeptide is represented by Seq. ID No. 10 and No. 16 in the Sequence Listing.

(Amino acid sequence of rat-derived FC99)

The amino acid sequence of the polypeptide of rat-derived FC99, estimated from the polynucleotide encoding the polypeptide of rat-derived FC99 whose base sequence has been determined in the foregoing manner, is represented by Seq. ID No. 11 and No. 17 in the Sequence Listing.

The rat FC99, like the human FC99, is found to show significant homology to the known Shc. That is, the polynucleotides of the PTB and SH2 domains are indicated as Seq. ID Nos. 12 and 14, respectively, in the Sequence Listing. The polypeptides of the PTB and SH2 domains based on them are indicated as Seq. ID Nos. 13 and 15, respectively, in the Sequence Listing.

The amino acid sequence translated from the determined base sequence shows significant homology to the known mouse Shc. Homologies for the amino acid sequences of the PTB and SH2 domains are 72.6% and 70.8%, respectively. (Rat FC99-containing transformed *E. coli*) A suitable strain of *E. coli* can be transformed with a clone containing the longest insert obtained above (see, for example, Cell Engineering Experiments Protocol (Shujunsha, 1991), 105–107).

*E. coli* transformed in the above-described fashion with pBluescriptSK⁻, plasmid containing a polynucleotide having the base sequence described as Seq. ID No. 16 in the Sequence Listing, was named pBS-R99, and deposited on Feb. 1, 1996 at the National Institute of Bioscience and Human Technology (1–3, Higashi 1-chome, Tsukuba-shi, Ibaraki-ken 305 JAPAN), Agency of Industrial Science and Technology, Ministry of International Trade and Industry (accession number: FERM P-15419). This transformant was transferred to international deposition on Sep. 25, 1996 (accession number: FERM BP-5672).

In the instant specification, the following abbreviations will be used, if desired.

| DNA | Dexoyribonucleic acid |
|---|---|
| A | Adenine |
| C | Cytosine |
| G | Guanine |
| T | Thymine |
| Ala (A) | Alanine |
| Arg (R) | Arginine |
| Asn (N) | Asparagine |
| Asp (D) | Aspartic acid |
| Cys (C) | Cysteine |
| Gln (Q) | Glutamine |
| Glu (E) | Glutamic acid |
| Gly (G) | Glycine |
| His (H) | Histidine |
| Ile (I) | Isoleucine |
| Leu (L) | Leucine |
| Lys (K) | Lysine |
| Met (M) | Methionine |
| Phe (F) | Phenylalanine |
| Pro (P) | Proline |
| Ser (S) | Serine |
| Thr (T) | Threonine |
| Trp (W) | Tryptophan |
| Tyr (Y) | Tyrosine |
| Val (V) | Valine |

The present invention will be described in detail based on the following working examples. However, these examples are offered by way of illustration, and do not limit the invention.

EXAMPLES

Example 1

Construction of human brain-derived uniformed cDNA library

A normalized cDNA library was constructed using human cerebral mRNA. Normalization was performed by the method of Sasaki et al. (DNA Research 1, 91–96, 1994) involving the steps (i), (ii) and (iii): (i) self hybridization in a semi-solid phase system, (ii) preparation of a phage cDNA library from mRNA treated in (i), and (iii) conversion from insert cDNA into cRNA. These steps were performed in the sequence (i), (ii), (iii), (i), (ii) to construct the normalized cDNA library.

Human FC99 gene cDNA cloning (1) Of 1 ml of the uniformed cDNA library constructed in the above manner, 100 μl was converted into a plasmid in accordance with in vivo excision (the method described in Stratagene's Uni-ZAP XR Cloning Kit Instruction Manual) using a helper phage (EXAssist helper phage, Stratagene).

More specifically, 200 μl of *E. coli* XL-1Blue, 100 μl of the uniformed cDNA library, and 1 μl of helper phage R408 (>1×10⁶ pfu/ml) were mixed in a 50 ml test tube, and the *E. coli* was infected with ZAP and the helper phage for 15 minutes at 37° C.

5 ml of 2xYT culture medium (10 g NaCl, 10 g Bacto Yeast Extract, 16 g Bactotryptone/11) was added, and the mixture was shake cultured for 3 hours at 37° C., causing the *E. coli* to secrete phagemid.

After heat treatment for 20 minutes at 70° C., centrifugation was performed for 5 minutes at 4000 g to eradicate the cells. The supernatant phagemid was transferred into another test tube.

This supernatant contained pBluescriptSK(–) particles. 200 microliters of this supernatant, or 20 μl of a 1:100 dilution of this supernatant was mixed with 200 μl of XL-1 Blue (OD600=1.0) for 15 minutes at 37° C. for infection.

The cultured medium (1 to 100 μl) was plated on LB/Amp plate, and cultured overnight at 37° C. The resulting colonies were E. coli (XL-1 Blue) transformants with double strand pBluescriptSK(−) containing the insert DNA.

(2) Plasmids were prepared from this E. coli by means of QIAwell 8 Plus kit (Qiagen).

(3) The sequences at the 5'-terminals of the inserts of the resulting plasmids were determined by Taq cycle sequencing (Biotechniques, 7, 494–499, 1989) using Perkin-Elmer's autosequencer 373A.

(4) The amino acid sequences obtained by translating the determined base sequences were compared with protein database (NBRF, Release 43) under the GENE-TYX program (Ver. 27, Software Development Co.) to analyze homology.

(5) The above-described sequence determination and homology analysis of more than 500 plasmids were performed. One plasmid containing the PTB domain and the SH2 domain was selected (designated as FC99; FC=forebrain cortex). For more detailed analysis, clones containing the whole of the region encoding the protein were isolated in the manner described below.

(6) Screening was performed using frontal cortex-derived cDNA library (Stratagene) and a part of the PTB domain of these clones (its base sequence is indicated as Seq. ID No. 9 in the Sequence Listing) as a probe.

A phage library solution (20 µl) and E. coli XL-1 Blue (200 µl) were cultured for 15 minutes at 37° C. The cultured medium was added to 2 to 3 ml of top agar (heated at 48° C.), and the mixture was plated on an NZY agar plate, and cultured overnight at 37° C.

About 50,000 plaques were cultured on each of six 100 mm square plates. These about 3×10$^5$ plaques were used for screening.

The NZY plate was cooled for 2 hours at 4° C., whereafter a nylon filter (HIGHBOND N+, Amersham) was placed on the plate, and allowed to stand for 2 minutes.

The nylon filter was peeled off, dried on a filter paper, and immobilized with UV rays to prepare a screening filter.

Hybridization was performed by the following procedure:

A probe for hybridization was a DNA fragment having the above-mentioned base sequence, the fragment being labeled with $^{32}$P-dCTP (Amersham) by means of a megaprime labeling kit (Amersham).

A prehybridization solution used contained 5×SSC (0.15M NaCl, 0.015M sodium citrate (pH 7.0)), 50% formamide, 1xdenhardt solution (0.2% bovine serum albumin (Fraction V), 0.2% polyvinyl pyrrolidone, 0.2% Ficoll400), 0.1% SDS, and 100 µg/ml salmon sperm DNA.

The filter was incubated in the prehybridization solution for 3 hours at 42° C., and incubated in a hybridization solution (the prehybridization solution containing 10% dextran sulfate) containing the labeled probe for 16 hours at 42° C. to perform hybridization.

Eight positive clones were obtained. The center of plaques of the positive ZAP phage clones in the resulting agar plates was dug out with a Pasteur pipette, and dissolved in a mixture of 500 µl SM buffer solution and 20 µl chloroform. The solution was vortex stirred, and then allowed to stand overnight.

200 µl of E. coli XL-1Blue, 200 µl of the positive phage clones (>1×10$^5$ phage particles), and 1 µl of helper phage R408 (>1×10$^6$ pfu/ml) were mixed in a 50 ml test tube, and the E. coli was infected with ZAP and the helper phage for 15 minutes at 37° C.

5 ml of 2×YT culture medium (10 g NaCl, 10 g Bacto Yeast Extract, 16 g Bactotryptone/11) was added, and the mixture was shake cultured for 3 hours at 37° C., causing the E. coli to secrete phagemid. The secretions were heat treated for 20 minutes at 70° C., and centrifuged for 5 minutes at 4000 g to eradicate the cells. The phagemid of the resulting supernatant was transferred into another test tube.

This supernatant contained pBluescript particles. 200 microliters of this supernatant, or 20 µl of a 1:100 dilution of this supernatant was mixed with 200 µl of XL-1 Blue (OD600=1.0) for 15 minutes at 37° C. for infection.

The cultured medium (1 to 100 µl) was plated on LB/Amp plates, and cultured overnight at 37° C. The resulting colonies were E. coli (XL-1 Blue) transformants with double stranded pBluescriptSK(−) containing the insert DNA.

Plasmids were prepared from the E. coli of the eight positive clones by means of a QIAprepPlasmid kit (Qiagen). For the clones with the longest insert (insert of about 2.5 kb), DNA base sequence determination was performed in the following manner:

(7) The base sequence of the 2.5 kb clone was determined by Taq cycle sequencing (Biotechniques, 7, 494–499, 1989) using Perkin-Elmer's autosequencer 373A. As a result, two sites were found feasible as the initiation point of translation. Of the analyzed base sequences of the cDNA's of FC99, 1425 bases starting at one of the initiation points of translation are indicated as Seq. ID No. 2 in the Sequence Listing, while 1785 bases starting at the other initiation point of translation are indicated as Seq. ID No. 8 in the Sequence Listing. The amino acid sequences encoded by the cDNA's are indicated as Seq. ID Nos. 1 and 7, respectively, in the Sequence Listing.

Analysis of FC99 gene-encoded amino acid sequences

The amino acid sequences translated from the determined base sequences contain two domains, PTB domain and SH2 domain, that are known to recognize phosphorylated tyrosine (its biochemical mechanisms are described, for example, in Heumann: Current opinion in Neurobiology, 4, 668–679, 1994, or Pawson: Nature, 373, 573–580, 1995), a known signal molecule in the signaling pathways in neurons of the brain (e.g., the signaling pathways in neurons where NGF acts) as shown in FIG. 2.

The structure of FC99 also closely resembles that of Shc, an adapter molecule in the intracellular signaling pathways, at the two sites, the PTB domain and the SH2 domain (see FIG. 1). Actually, homology for the PTB domain is 77.4%, and homology for the SH2 domain is 67.7%. Furthermore, tyrosine residues to be phosphorylated (Shc has been shown to bind Grb2, another adapter molecule, via this phosphorylated tyrosine), a tool indispensable for Shc to act as an adapter molecule in intracellular signaling pathways, are well retained between FC99 and Shc.

Example 2

Comparison of the level of expression of the FC99 gene among 16 kinds of cells

This comparison was made by northern blotting in accordance with the method described in Molecular Cloning, A Laboratory Manual, 2nd ed., Cold Spring Harbor Laboratory Press, 7.39–7.52, 1989. Human multiple tissue northern blots (Clontech) were produced by agarose electrophoresing polyA+RNA, extracted from 2 µg each of the heart, brain, placenta, lung, liver, skeletal muscle, kidney and pancreas, and then transferring the electrophoresed products onto a membrane. Human multiple tissue northern blots II (Clontech) were produced by agarose electrophoresing polyA+RNA, extracted from 2 µg each of the spleen, thymus, testicle, prostate, ovary, small intestine, large intestine, and peripheral lymphocytes, and then transferring the electrophoresed products onto a membrane.

A probe for hybridization was a DNA fragment having the base sequence described as Seq. ID No. 9 in the Sequence Listing, the fragment being labeled with 32P-dCTP (Amersham) by means of a megaprime labeling kit (Amersham).

A prehybridization solution used contained 50% formamide, 5xdenhardt solution (1% bovine serum albumin (Fraction V), 1% polyvinyl pyrrolidone, 1% Ficoll400), 0.5% SDS, 5×SSC (0.15M NaCl, 0.015M sodium citrate (pH 7.0)), and 100 μg/ml salmon sperm DNA.

The filter was incubated in the prehybridization solution for 3 hours at 42° C., and incubated in a hybridization solution (a solution of the same composition as the prehybridization solution) containing the labeled probe for 16 hours at 42° C. to perform hybridization.

After washing, the membrane was placed for 2 days at −80° C. in intimate contact with an X-ray film, and then developed. The results of quantitative determination of the densities of the respective bands on the X-ray film by means of a densitometer are shown in FIG. 2.

Example 3
Production of anti-FC99 antibody

The production of the antibody was performed in the following manner in accordance with the method described in Chapter 5 of "Antibodies: A Laboratory Manual" (Cold Spring Harbor Laboratory Press, 1988):

Two peptides included in both of the amino acid sequences described as Seq. ID. Nos. 1 and 7 in the Sequence Listing, (I) PWTEEEGDGSDHPYYN (the sequence as Seq. ID. No. 18 in the Sequence Listing) and (II) QTPLRQGSSDIYSTP (the sequence as Seq. ID. No. 19 in the Sequence Listing), were each synthesized in the form of having cysteine added to the C-terminus, and conjugated to a carrier protein, KLH (Keyhole Limpet Hemocyanin), by the MCS (heterocrosslinking reagent) method. Then, the rabbit was immunized twice with the conjugation product at an interval of 2 weeks. Blood samples were taken 5 and 6 weeks after the initial immunization, and measured for the antibody titer by the ELISA method using the peptide used in the immunization. With each of the peptides I and II, the antibody titer increased more than 16,000-fold at 6 weeks. At this time, antiserum (antibody) was collected in a large amount, and a part of the antiserum was used in experiments of Example 4.

Example 4
Detection of FC99 protein by anti-FC99 antibody

Figure 3:
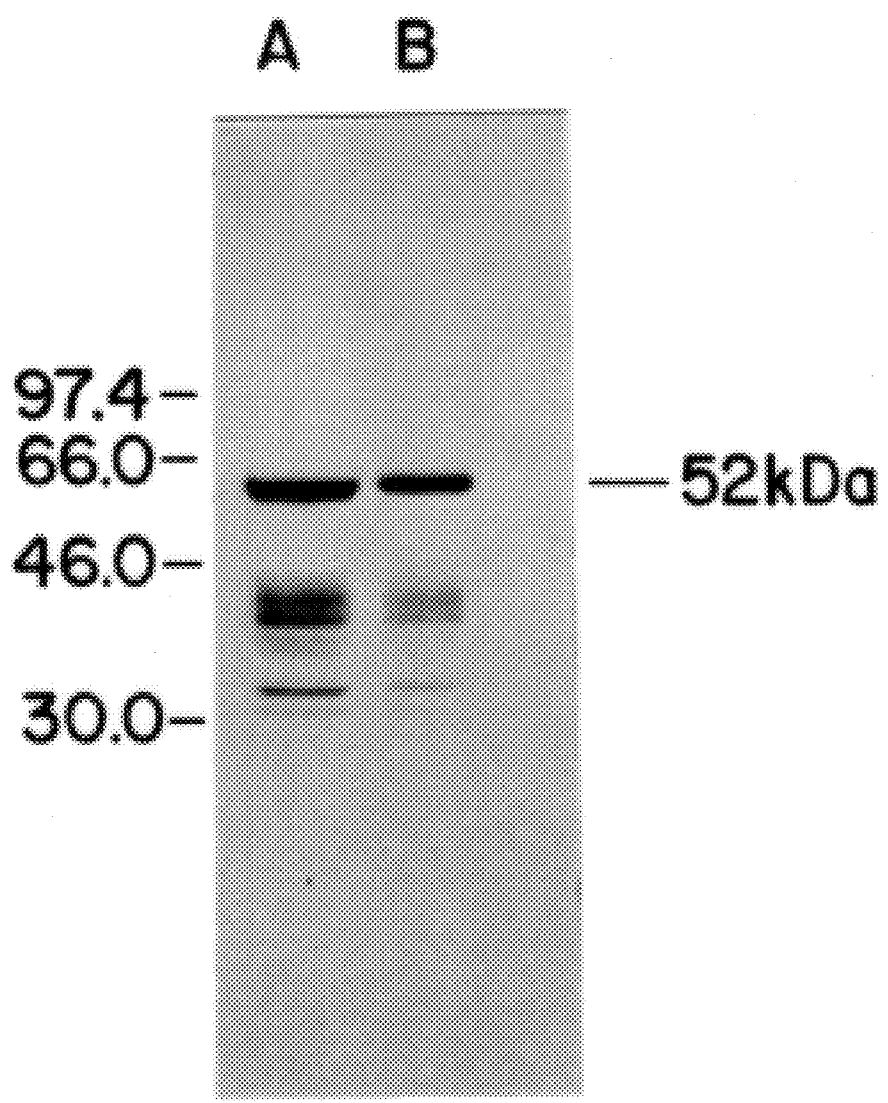
FIG. 3 is a photograph showing the results of detection of FC99 protein by western blotting using anti-FC99 antibody, FIG. 3 lane A and lane B corresponding to peptides I and II, respectively, of Example 3, both having a band at 52 kDa (indicated by the arrow)
Figure 4A:
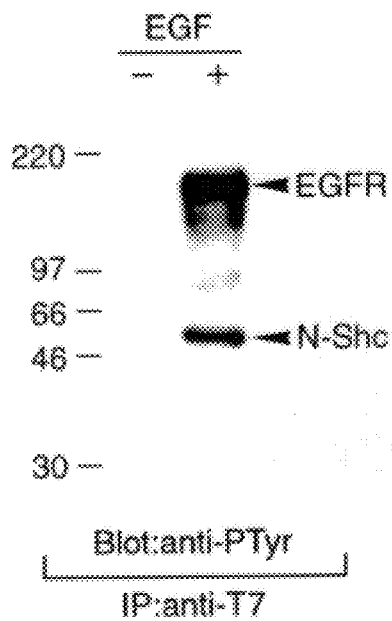
FIG. 4 is a photograph showing the results of detection of the effect of EGF on T7 peptide-added FC99 protein, expressed in COS-1 cells, by western blotting using part (A) anti-phosphorylated tyrosine antibody, part (B) anti-EGF receptor antibody, part (C) anti-Grb2 antibody, and part (D) anti-T7 peptide antibody. The numerals on the left denote molecular weights in kDa.
Figure 4B:
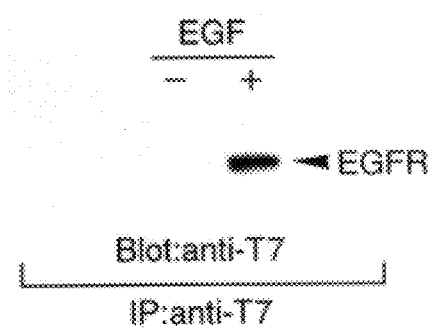
Figure 4C:
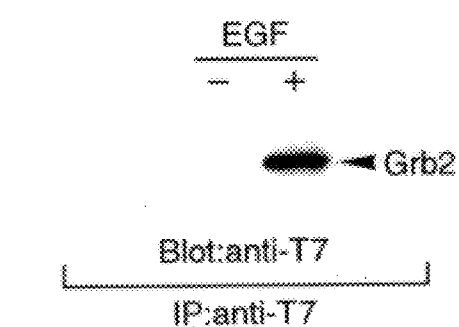
Figure 4D:
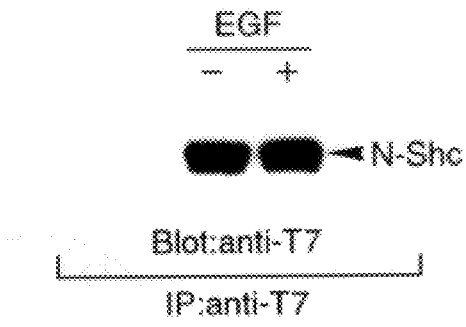
Figure 5A:
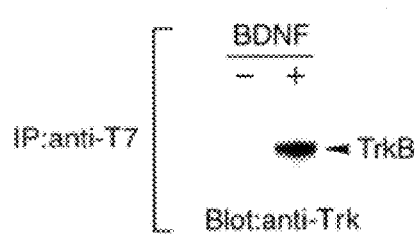
FIG. 5 is a photograph showing the results of detection of the effect of BDNF on the expression of T7 peptide-added FC99 protein in NIH3T3 cells by western blotting using part (A) anti-TrK receptor antibody, part (B) and part (D) anti-phosphorylated tyrosine antibody, part (C) and part (F) anti-T7 receptor antibody, and part (E) anti-Grb2 antibody; A to C being designed to study responses to BDNF in NIH3T3 cells incorporating both a plasmid expressing TrkB receptor and a plasmid expressing T7 peptide-added FC99 protein; parts D to F revealing the results of investigation in which the behaviors of T7 peptide-added FC99 protein in the presence and absence of BDNF and in the presence and absence of BDNF receptor (TrkB) were investigated by western blotting using part (D) anti-phosphorylated tyrosine antibody, part (E) anti-Grb2 antibody, and part (F) anti-T7 peptide antibody; and G showing the results of calibration on the photograph of part D by means of a scanner.
Figure 5D:
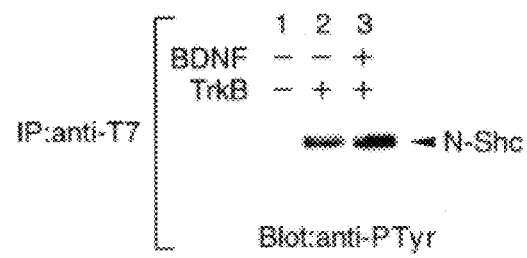
Figure 5B:
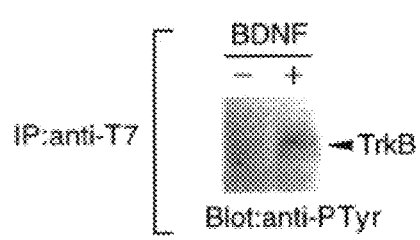
Figure 5E:
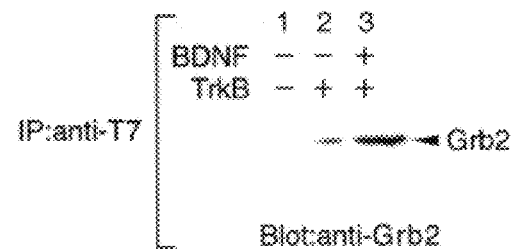
Figure 5C:
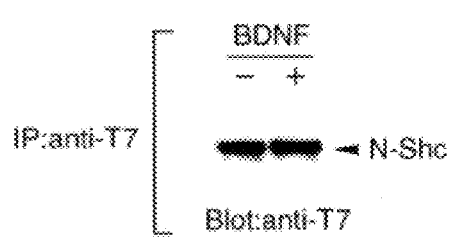
Figure 5F:
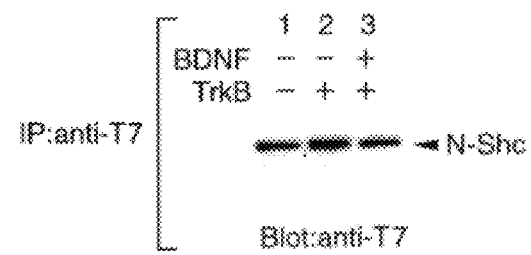
Figure 5G:
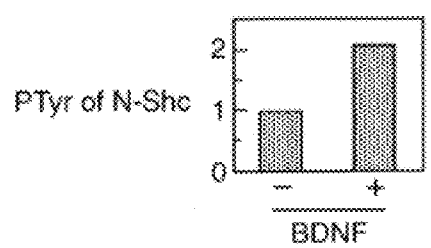

A base sequence encoding the amino acid sequence described as Seq. ID No. 1 in the Sequence Listing was inserted between the HindIII site and the XbaI site of the pRc/CMV plasmid (Invitrogen). The plasmid was introduced into COS-1 cells using LipofectAmine (Gibco-BRL) (the introduction followed the manual attached to the LipofectAmine). After 48 hours of culture, a cell extract was prepared (this cell extract would contain a polypeptide corresponding to the amino acid sequence described as Seq. ID No. 1 in the Sequence Listing). The cell extract was electrophored on a polyacrylamide gel, and analyzed by western blotting using the two kinds of antibodies prepared in Example 3. In both cases, bands corresponding to the FC99 protein having the amino acid sequence described as Seq. ID No. 1 were detected at the position of 52 kDa (the bands by the antibodies based on the peptides I and II of Example 3 are shown in FIG. 3 parts A and, the band for 52 kDa being shown by the arrow in the drawing). The analyses by western blotting followed the method described in Chapter 12 of "Antibodies: A Laboratory Manual" (Cold Spring Harbor Laboratory Press, 1988).

Example 5
Involvement of FC99 protein in signal transmission of epidermal growth factor (1) A base sequence was prepared by adding a base sequence, which encodes T7 peptide (Met-Ala-Ser-Met-Thr-Gly-Gly-Gln-Gln-Met-Gly) (the sequence as Seq. ID No. 20 in the Sequence Listing), to the 5'-terminus of a base sequence encoding the amino acid sequence described as Seq. ID No. 1 in the Sequence Listing. The resulting base sequence was inserted between the HindIII site and the Xba I site of the pRc/CMV plasmid (Invitrogen).

(2) For use in immunoprecipitation, anti-T7 peptide antibody (Novagen) was covalently bonded to protein A-Sepharose (Pharmacia) in accordance with the method described on pages 521 to 523 of "Antibodies Laboratory Manual".

(3) The plasmid prepared in (1) was introduced into COS-1 cells by use of LipofectAmine (Gibco-BRL) in accordance with a manual attached to the LipofectAmine to express T7 peptide-added FC99 protein having T7 peptide added to the N-terminal of the amino acid sequence described as Seq. ID No. 1 in the Sequence Listing. After 18 hours of culture under low serum content conditions, EGF was administered to a concentration of 100 ng/ml (for control, no EGF was administered). Five minutes after EGF administration, a cell extract was prepared. The extract was immunoprecipitated using the anti-T7 peptide antibody covalently bonded to the protein A-Sepharose prepared in (2). This procedure was performed in accordance with an example described in Oncogene (1995), 11, 899–907.

(4) The immunoprecipitate was electrophoresed on a polyacrylamide gel, and then analyzed by western blotting using (A) anti-phosphorylated tyrosine antibody, (B) anti-EGF receptor antibody, (C) anti-Grb2 antibody, and (D) anti-T7 peptide antibody. The results are shown in FIG. 4. parts B to D show only bands close to the colored regions. As shown in FIG. 4 part A, tyrosine phosphorylation of FC99 (N-Shc) occurred only when stimulated with EGF. On this occasion, another phosphorylated band appeared near 180 KDa. This band was found to be EGF receptor as shown in FIG. 4 part B. FIG. 4 part C also showed that FC99 and the adapter molecule Grb2 were joined together depending on stimulation with EGF. As seen in FIG. 4 part D, the amount of the immunoprecipitated T7 peptide-added FC99 protein did not change with the presence or absence of EGF. These findings demonstrated that EGF receptor activated by the administration of EGF bound FC99 to tyrosine phosphorylate the FC99, inducing the joining of the FC99 and the Grb2. Based on this fact, Grb2/SOS complex migrates close to the cell membrane, arousing the activation of ras by SOS.

Example 6
Cloning of rat FC99 gene cDNA (1) Screening was performed in the same manner as in Example 1(6) by using rat brain-derived cDNA library (Stratagene) and a part of the base sequence of human FC99 gene (the base sequence is indicated as Seq. ID No. 9 in the Sequence Listing) as a probe.

Plasmids were prepared from the E. coli of the five positive clones of the resulting E. coli (XL-1 Blue) transformants by means of a QIAprepPlasmid kit (Qiagen). For the clones with the longest insert (insert of about 4.1 kb), DNA base sequence determination was performed in the following manner:

(2) The base sequence of the resulting 4.1 kb clone was determined by Taq cycle sequencing (Biotechniques, 7, 494–499, 1989) using Perkin-Elmer's DNA sequencer 373A. As a result, two sites were found feasible as the initiation point of translation. Of the analyzed base sequences of the cDNA's of rat FC99, 1425 bases starting at one of the initiation points of translation are indicated as Seq. ID No. 10 in the Sequence Listing, while 1785 bases starting at the other initiation point of translation are indicated as Seq. ID No. 16 in the Sequence Listing. The amino acid sequences encoded by the cDNA's are indicated as Seq. ID Nos. 11 and 17, respectively, in the Sequence Listing.

Example 7

Involvement of FC99 protein in signal transmission of brain-derived neurotrophic factor BDNF (1) A base sequence was prepared by adding a base sequence, which encodes T7 peptide (Met-Ala-Ser-Met-Thr-Gly-Gly-Gln-Gln-Met-Gly), to the 5'-terminus of a base sequence encoding the amino acid sequence described as Seq. ID No. 1 in the Sequence Listing. The resulting base sequence was inserted between the Hind III site and the Xba I site of the pRc/CMV plasmid (Invitrogen).

(2) For use in immunoprecipitation, anti-T7 peptide antibody (Novagen) was covalently bonded to protein A-Sepharose (Pharmacia) in accordance with the method described on pages 521 to 523 of "Antibodies Laboratory Manual".

(3) only the plasmid prepared in (1), or the plasmid prepared in (1) together with the same amount of an expression vector for BDNF receptor (TrkB receptor, or simply TrkB), was introduced into NIH3T3 cells by use of the LipofectAmine (Gibco-BRL) in accordance with a manual attached to the LipofectAmine to express T7 peptide-added FC99 protein receptor having T7 peptide added to the N-terminal of the amino acid sequence described as Seq. ID No. 1 in the Sequence Listing or TrkB. After 18 hours of culture under low serum content conditions, BDNF was administered to a concentration of 100 ng/ml (for control, no BDNF was administered). Five minutes after BDNF administration, a cell extract was prepared. The extract was immunoprecipitated using the anti-T7 peptide antibody covalently bonded to the protein A-Sepharose prepared in (2). This procedure was performed in accordance with an example described in Oncogene (1995), 11, 899–907.

(4) The immunoprecipitate was electrophoresed on a polyacrylamide gel. Then, the immunoprecipitate from the cells incorporating both the plasmid prepared in (1) and the BDNF receptor expression vector was analyzed by western blotting using (A) anti-Trk receptor antibody, (B) anti-phosphorylated tyrosine antibody, and (C) anti-T7 peptide antibody. The results are shown in FIG. 5. As shown in FIG. 5 part A, TrkB was bound to FC99 only when stimulated with BDNF. Also, as shown in FIG. 5 part B, tyrosine phosphorylation of the TrkB receptor occurred upon stimulation with BDNF. As seen in FIG. 5 part C, the amount of the immunoprecipitated T7 peptide-added FC99 protein did not change with the presence or absence of BDNF. Likewise, analysis by western blotting was made using (D) anti-phosphorylated tyrosine antibody, (E) anti-Grb2 antibody, and (F) anti-T7 peptide antibody. The results are shown in FIG. 5 parts D to F. Lane 1 gives the results on the immunoprecipitate from the cells incorporating only the peptide prepared in (1) but not administered BDNF. Lane 2 offers the results on the immunoprecipitate from the cells incorporating the peptide prepared in (1) and TrkB, but not administered BDNF. A comparison between Lanes 2 and 3 in FIG. 5 parts D to F showed that tyrosine phosphorylation of the FC99 protein, and the binding of the FC99 protein and Grb2 increased depending on BDNF. The amount of the BDNF-dependent increase in the tyrosine phosphorylation of the FC99 protein was investigated by reading the photograph of FIG. 5 part D into a scanner (Model GT-6000, Epson), and comparing the densities of Lanes 2 and 3 by means of the NIH Image (an image analysis software of NIH, U.S.A.). The results, as in FIG. 5 part G, showed about 2-fold increase dependent on the administration of BDNF. A comparison of Lanes 1 and 2 in FIG. 5 parts D and E showed that the tyrosine phosphorylation of FC99 protein and the binding of FC99 protein and Grb2 in the absence of BDNF took place by the action of the TrkB receptor introduced together with the plasmid prepared in (1). These findings demonstrated that the TrkB receptor activated by the administration of BDNF formed a complex of the tyrosine-phosphorylated FC99 protein with Grb2. Based on this fact, the Grb2/SOS complex migrates close to the cell membrane, arousing the activation of ras by SOS.

Activation of ras by SOS is known to promote the growth of nerve cells (Rozakis-Adcock et al., Nature 360, 689–692, 1992). Thus, the polypeptides and polynucleotides of the present invention are expected to be useful for the diagnosis and treatment of diseases in which nerve cells are involved.

From the invention thus described, it will be obvious that the invention may be varied in many ways. Such variations are not to be regarded as a departure from the spirit and scope of the invention, and all such modifications as would be obvious to one skilled in the art are intended for inclusion within the scope of the following claims.

The basic Japanese Application Nos. 265988/1995 filed on Oct. 13, 1995, 323069/1995 filed on Dec. 12, 1995, 069265/1996 filed on Feb. 29, 1996, and 212973/1996 filed on Jul. 24, 1996 are hereby incorporated by reference.

What is claimed is:

1. A polypeptide comprising at least an amino acid sequence described as Seq. ID No. 1 in the Sequence Listing.

2. A polypeptide comprising at least an amino acid sequence described as Seq. ID No. 7 in the Sequence Listing.

3. A polypeptide comprising at least an amino acid sequence described as Seq. ID No. 3 in the Sequence Listing.

4. A polypeptide comprising at least an amino acid sequence described as Seq. ID No. 5 in the Sequence Listing.

5. A polypeptide comprising an amino acid sequence described as SEQ ID No. 3 in the Sequence Listing covalently linked via non-specific amino acids to an amino acid sequence described as SEQ ID No. 5 in the Sequence Listing.

6. A polypeptide comprising at least an amino acid sequence described as Seq. ID No. 11 in the Sequence Listing.

7. A polypeptide comprising at least an amino acid sequence described as Seq. ID No. 17 in the Sequence Listing.

8. A polypeptide comprising at least an amino acid sequence described as Seq. ID No. 13 in the Sequence Listing.

9. A polypeptide comprising at least an amino acid sequence described as Seq. ID No. 15 in the Sequence Listing.

10. A polypeptide comprising an amino acid sequence described as SEQ ID No. 13 in the Sequence Listing covalently linked via non-specific amino acids to an amino acid sequence described as SEQ ID No. 15 in the Sequence Listing.

11. A polypeptide comprising an amino acid sequence described as SEQ ID No. 21 in the Sequence Listing.

12. A polypeptide comprising an amino acid sequence described as SEQ ID No. 22 in the Sequence Listing.

* * * * *